US011648295B2

(12) United States Patent
Pereira

(10) Patent No.: US 11,648,295 B2
(45) Date of Patent: May 16, 2023

(54) METHODS OF TREATING DISEASES RESULTING FROM A MALADAPTED STRESS RESPONSE

(71) Applicant: Cortene Inc., Burlingame, CA (US)

(72) Inventor: Gerard Pereira, Burlingame, CA (US)

(*) Notice: Subject to any disclaimer, the term of this patent is extended or adjusted under 35 U.S.C. 154(b) by 0 days.

(21) Appl. No.: 16/389,683

(22) Filed: Apr. 19, 2019

(65) Prior Publication Data

US 2019/0307844 A1 Oct. 10, 2019

Related U.S. Application Data

(63) Continuation of application No. PCT/US2017/057736, filed on Oct. 20, 2017.

(60) Provisional application No. 62/410,764, filed on Oct. 20, 2016.

(51) Int. Cl.
*A61K 38/17* (2006.01)
*A61K 38/16* (2006.01)

(52) U.S. Cl.
CPC .......... *A61K 38/1796* (2013.01); *A61K 38/16* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2002/0035083 A1 | 3/2002 | Ho | |
| 2003/0148956 A1 | 8/2003 | Isfort et al. | |
| 2003/0148958 A1* | 8/2003 | Isfort | A61P 21/00 514/10.8 |
| 2003/0165807 A1 | 9/2003 | Isfort et al. | |
| 2004/0063630 A1 | 4/2004 | Schreiner | |
| 2004/0204564 A1* | 10/2004 | Rivier | A61P 25/22 530/350 |
| 2015/0309050 A1 | 10/2015 | May | |
| 2019/0307844 A1* | 10/2019 | Pereira | A61P 37/06 |

FOREIGN PATENT DOCUMENTS

| | | | |
|---|---|---|---|
| JP | 2013510167 | * | 3/2013 |
| WO | 97/00063 | | 1/1997 |

OTHER PUBLICATIONS

Funk "A CRF2 agonist administered into the central nucleus of the amygdala decreases ethanol self-administration in ethanol dependent rats" 172-178. BrainRes. Jun. 25, 2007; Abstract, p. 4; DOI:10.1016/j.brainres.2007.04.009.*
Int'l Search Report and Written Opinion received in copending PCT Application No. PCT/US2017/057736 dated Apr. 12, 2018, 6 pages.
Haney et al., Diagnostic Methods for Myalgic Encephalomyelitis/Chronic Fatigue Syndrome: A Systematic Review for a National Institutes of Health Pathways to Prevention Workshop. Annals of Internal Medicine. Jun. 16, 2015, vol. 162, No. 12, pp. 834-840. p. 836, Table; Appendix Table 2.
Henningsen et al., Management of functional somatic syndromes. Lancet, Feb. 6, 2007, vol. 369, pp. 946-955. p. 948, col. 2, para 1: p. 950, Table 2.
Murakami et al., Psychosomatic Aspects of Fibromyalgia. In: Koh K. (eds) Somatization and Psychosomatic Symptoms (2013) Springer, New York, NY. Chapter 13, pp. 165-174. p. 165, para 2; p. 170, para 1.
Abbruzzese et al., Tonic vibration reflex in Holmes-Adie syndrome: an electrophysiological study. Journal of Neurology, Neurosurgery, and Psychiatry, 1979, vol. 42, pp. 943-947. Abstract.
Lafreniere et al., Identification of a Novel Gene (HSN2) Causing Hereditary Sensory and Autonomic Neuropathy Type II through the Study of Canadian Genetic Isolates. Am. J. Hum. Genet.2004. vol. 74, pp. 1064-1073. p. 1065, col. 1, para 3.
Jankovic Parkinson?s disease: clinical features and diagnosis. J Neurol Neurosurg Psychiatry 2008, vol. 79, pp. 368-376. Abstract; p. 368, col. 2, para 1; p. 369, col. 2, para 3.
Louthrenoo et al., Cardiovascular autonomic nervous system dysfunction in patients with rheumatoid arthritis and systemic lupus erythematosus. QJM: An International Journal of Medicine, Feb. 1, 1999, vol. 92, Issue 2, pp. 97-102. Abstract.
European Search Report and Opinion received in copending EP Application No. 17862092.8 dated Jul. 7, 2020, 24 pages.
Montecucchi P C et al: "Amino Acid Composition and Sequence Analysis of Sauvagine, A New Active Peptide From the Skin of Phyllomedusa Sauvage", International Journal of Peptide and Protein Research, Munksgaard, Copenhagen, DK, vol. 18, Aug. 1, 1981 (Aug. 1, 1981), pp. 113-120, XP000881992, ISSN: 0367-8377.
Million M et al: "Peripheral injection of sauvagine prevents repeated colorectal distension-induced visceral pain in female rats", Peptides, Elsevier, Amsterdam, NL, vol. 26, No. 7, Jul. 1, 2005 (Jul. 1, 2005), pp. 1188-1195, XP027856526, ISSN: 0196-9781 [retrieved on Jul. 1, 2005].
Glenn R. Valdez et al: "Increased Anxiety-Like Behavior and Ethanol Self-Administration in Dependent Rats: Reversal via Corticotropin-Releasing Factor-2 Receptor Activation", Alcoholism: Clinical and Experimental Research., vol. 28, No. 6, Jun. 1, 2004 (Jun. 1, 2004), pp. 865-872, XP055679542, us ISSN: 0145-6008, DOI:10.1097/01.ALC.0000128222.29875.40.

(Continued)

*Primary Examiner* — Maury A Audet
(74) *Attorney, Agent, or Firm* — Womble Bond Dickinson (US) LLP

(57) ABSTRACT

The present invention relates to methods for reversing maladaptations involving the corticotropin-releasing factor receptor subtype 2 (CRFR2). It is postulated that in functional somatic syndrome (FSS), a group of diseases with overlapping symptoms, including systemic exertion intolerance disease (SEID, also known as chronic fatigue syndrome or myalgic encephalomyelitis), and several others, this receptor is up-regulated and relocated to the neuronal membranes of key regions of the brain including the raphe nuclei, the limbic system and the cortex. This configuration leads to a dysfunctional stress response. According to one embodiment of the invention, a method for reversing CRFR2 maladaptations includes the sustained stimulation of the receptor over a period of time to bring about a persistent receptor endocytosis, resulting in measurable symptom improvement.

11 Claims, 8 Drawing Sheets

Specification includes a Sequence Listing.

(56) References Cited

OTHER PUBLICATIONS

Demitrack M A et al: "Evidence for impaired activation of the hypothalamic-pituitary-adrenal axis in patients with chronic fatigue syndrome", Journal of Clinical Endocrinology and Metabolism, The Endocrine Society, US, vol. 73, No. 6, Dec. 1, 1991 (Dec. 1, 1991), pp. 1224-1234, XP009154276, ISSN: 0021-972X, DOI:10.1210/JCEM-73-6-1224.

L. V. Scott et al: "Blunted adrenocorticotropin and Cortisol responses to corticotropin-releasing hormone stimulation in chronic fatigue syndrome", Acta Psychiatrica Scandinavica., vol. 97, No. 6, Jun. 1, 1998 (Jun. 1, 1998), pp. 450-457, XP055679879, DE ISSN: 0001-690X, DOI:10.1111/j.1600-0447.1998.tb10030.x.

Goertzel Benjamin N et al: "Combinations of single nucleotide polymorphisms in neuroendocrine effector and receptor genes predict chronic fatigue syndrome", Pharmacogenomics, Future Medicine, UK, vol. 7, No. 3, Apr. 1, 2006 (Apr. 1, 2006), pp. 475-483, XP002587130, ISSN: 1462-2416, DOI:10.2217/14622416.7.3.475.

Tracy L. Bale et al: "Role in Stress Responsivity and Other Behaviors", Annual Review of Pharmacology and Toxicology, vol. 44, No. 1, Feb. 10, 2004 (Feb. 10, 2004), pp. 525-557, XP055679895, us ISSN: 0362-1642, DOI: 10.1146/annurev.pharmtox.44.101802.121410.

Mazur A W et al: "Sauvagine analogs selective for corticotropin releasing factor 2 receptor: effect of substitutions at positions 35 and 39 on CRF2R selectivity", Peptides, Elsevier, Amsterdam, NL, vol. 26, No. 5, May 1, 2005 (May 1, 2005), pp. 887-891, XP027856581, ISSN: 0196-9781 [retrieved on May 1, 2005].

Cleare, A.J. et al., Hypothalamo-Pituitary-Adrenal Axis Dysfunction in Chronic Fatigue Syndrome, and the Effects of Low-Dose Hydrocortisone Therapy, The Journal of Clinical Endocrinology & Metabolism 86(8), 2001 by the Endocrine Society.

Demitrack, Mark A. et al., Evidence for Impaired Activation of the Hypothalamic-Pituitary-Adrenal Axis in Patients with Chronic Fatigue Syndrome, The Journal of Clinical Endocrinology & Metabolism, vol. 73, Issue 6, Dec. 1, 1991.

Deussing, Jan M. et al., The Corticotropin-Releasing Factor Family: Physiology of the Stress Response, 2018 by the American Physiological Society.

Papadopoulos, Andrew S., et al., Hypothalamic-pituitary-adrenal axis dysfunction in chronic fatigue syndrome, Nat. Rev. Endocrinol. 8, 22-32 (2012).

Tanriverdi, F. et al., The hypothalamo-pituitary-adrenal axis in chronic fatigue syndrome and fibromyalgia syndrome, Informa Healthcare, Department of Endocrinology, Medical School, Erciyes University, Kayseri, Turkey, Mar. 2007.

Tomas, Cara et al., A Review of Hypothalamic-Pituitary-Adrenal Axis Function in Chronic Fatigue Syndrome, Hindawi Publishing Corporation ISRN Neuroscience, 2013.

Office Action for Japanese Patent Application No. 2019-543179, dated Sep. 17, 2021.

Japanese Journal of Psychosomatic Medicine, Functional Somatic Syndromes—Analytical Thinking and Holistic Thinking, 53(12) (2013).

Twisk, Frank N.M., Replacing Myalgic Encephalomyelitis and Chronic Fatigue Syndrome with Systemic Exercise Intolerance Disease is Not the Way Forward, Diagnostics 6(1) (Feb. 2016).

Davis, Mark E. et al., Urocortin 2 Infusion in Healthy Humans, Journal of the American College of Cardiology 49(4) (2007).

Oliveira, Leandro A. et al., Pharmacological Research 95-96 (2015).

Mackay, Kenneth B., Effects of a Selective Agonist and Antagonist of CRF2 Receptors on Cardiovascular Function in the Rat, European Journal of Pharmacology 469 (2003).

Chen, Chih-Yen et al., Intravenous Urocortin II Decreases Blood Pressure Through CFR2 Receptor in Rats, Regulatory Peptides 113 (2003).

Martinez, Vicente et al., Central CFR, Urocortins and Stress Increase Colonic Transit via CRF1 Receptors While Activation of CRF2 Receptors Delays Gastric Transit in Mice, Journal of Physiology 556(1) (2004).

Jones, Declan N.C. et al., The Behavioural Effects of Corticotropin-Releasing Factor-Related Peptides in Rats, Psychopharmacology 138 (1998).

De Groote, Lotte et al., Differential Monoaminergic, Neuroendocrine and Behavioural Responses After Central Administration of Corticotropin-Releasing Factor Receptor Type 1 and 2 Agonists, Journal of Neurochemistry 94 (2005).

International Search Report and Written Opinion for PCT/US22/71209, dated Jul. 28, 2022.

\* cited by examiner

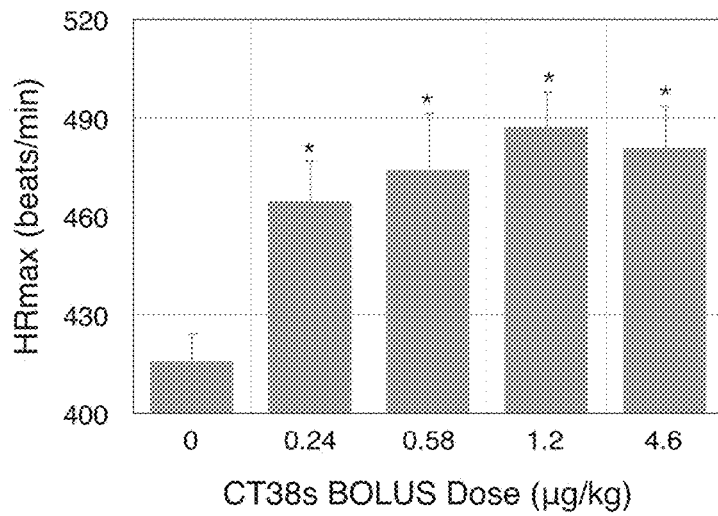

FIGURE 1A: Effect of subcutaneous bolus doses of CT38s on maximum heart rate (HRmax) in normal rats (* $p < 0.05$ versus control).

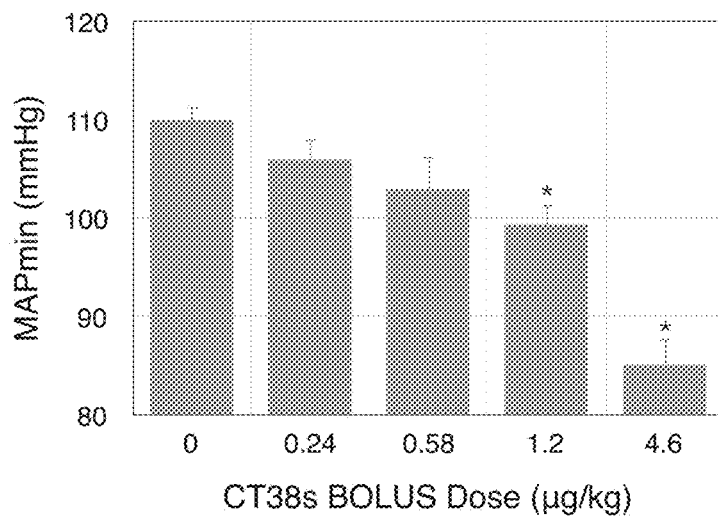

FIGURE 1B: Effect of subcutaneous bolus doses of CT38s on minimum mean arterial pressure (MAPmin) in normal rats (* $p < 0.05$ versus control).

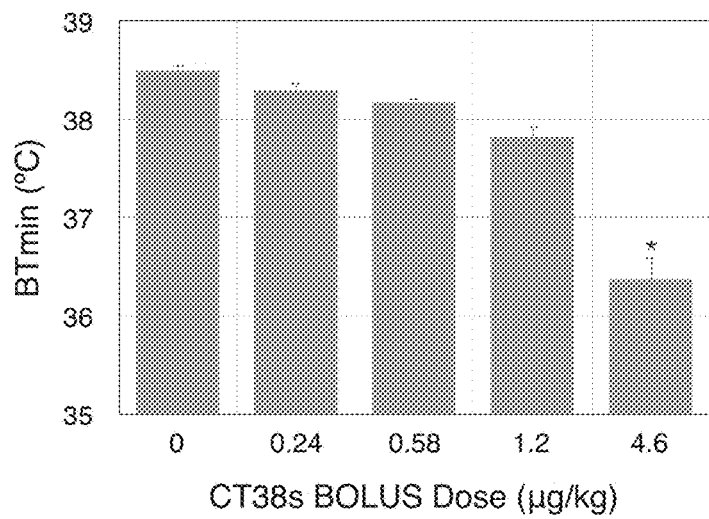

FIGURE 1C: Effect of subcutaneous bolus doses of CT38s on minimum body temperature (BTmin) in normal rats (* $p < 0.05$ versus control).

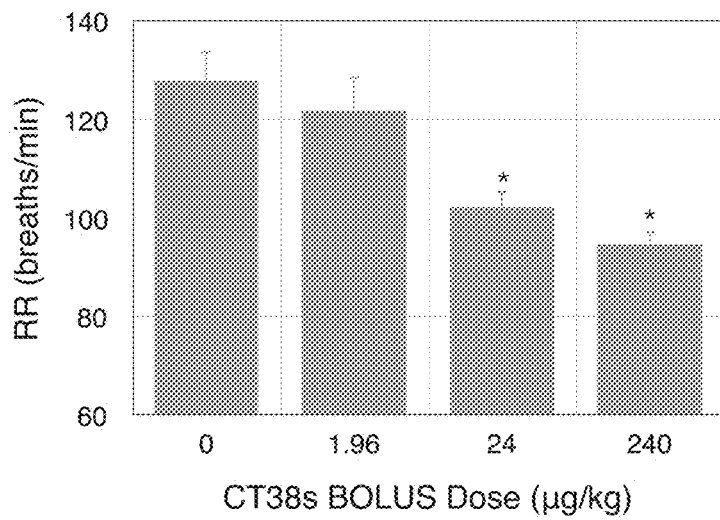
FIGURE 2: Effect of subcutaneous bolus doses of CT38s on respiratory rate (RR) in normal rats (* $p < 0.05$ versus control).
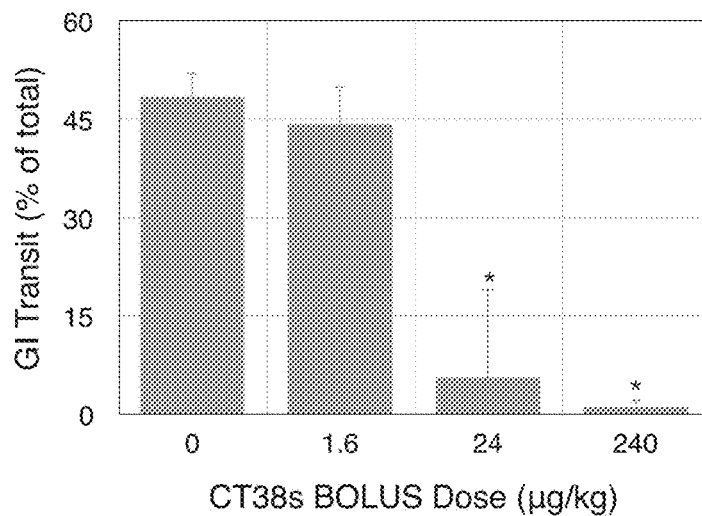
FIGURE 3: Effect of subcutaneous bolus doses of CT38s on gastrointestinal (GI) transit in normal rats (* $p < 0.05$ versus control).
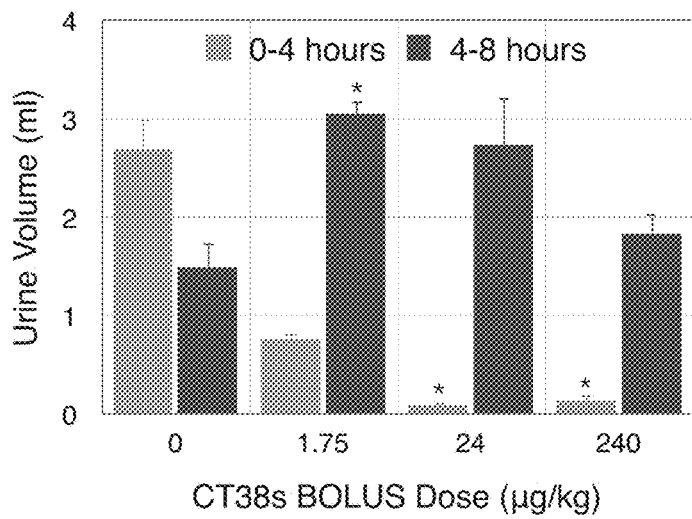
FIGURE 4: Effect of subcutaneous bolus doses of CT38s on urine volume at 0-4 hours and 4-8 hours in normal rats (* $p < 0.05$ versus control).

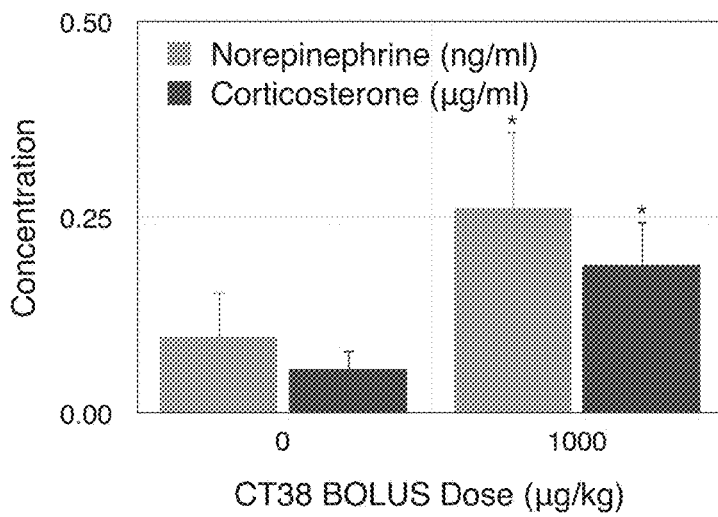

FIGURE 5: Effect of subcutaneous bolus doses of CT38 on norepinephrine and corticosterone secretion in normal rats (* $p < 0.05$ versus control).

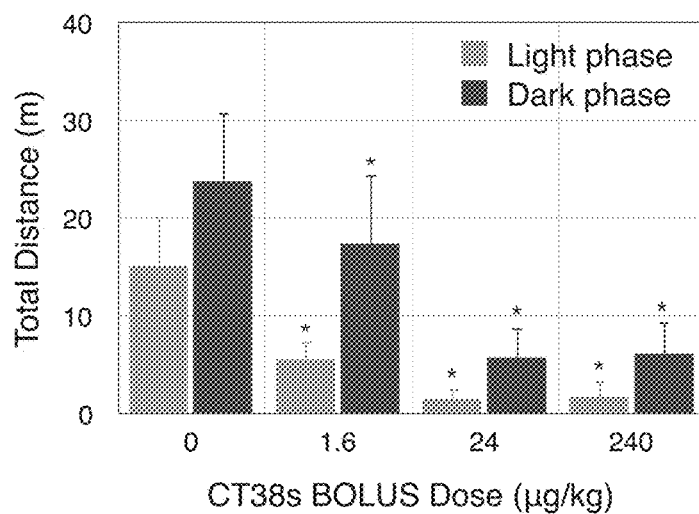

FIGURE 6A: Effect of subcutaneous bolus doses of CT38s on total distance traveled during light and dark in normal rats (* $p < 0.05$ versus control).

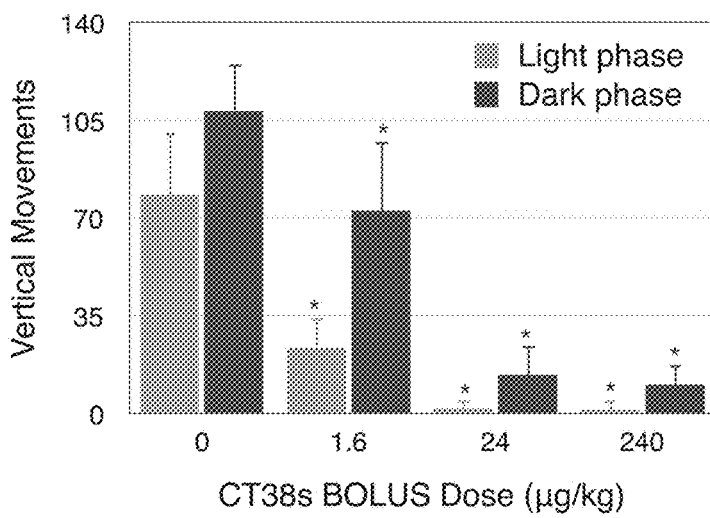

FIGURE 6B: Effect of subcutaneous bolus doses of CT38s on number of vertical movements during light and dark in normal rats (* $p < 0.05$ versus control).

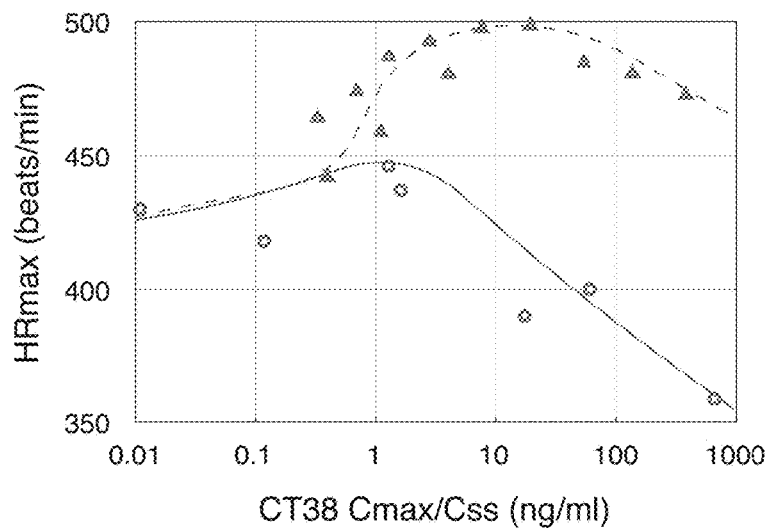

FIGURE 7A: Effect of maximum or steady state plasma concentrations (Cmax or Css) of CT38, dosed subcutaneously by bolus (triangles, dashed line) or infusion (circles, solid line), on the maximum heart rate (HRmax) in normal rats.

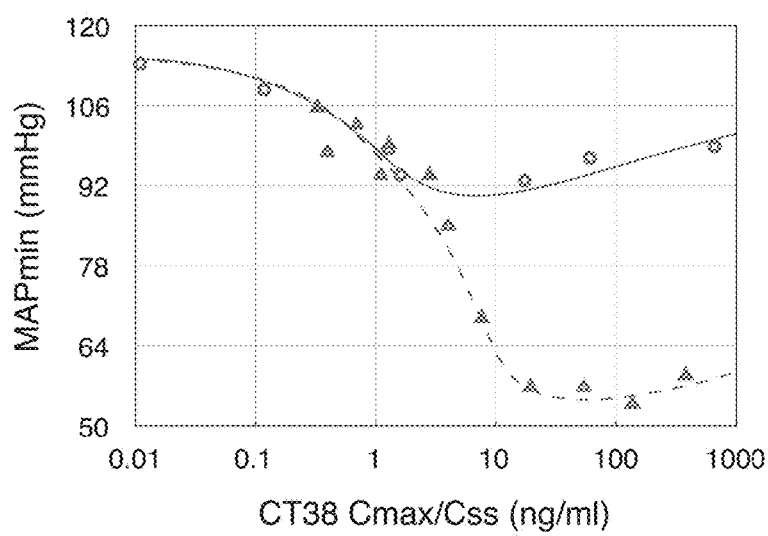

FIGURE 7B: Effect of maximum or steady state plasma concentrations (Cmax or Css) of CT38, dosed subcutaneously by bolus (triangles, dashed line) or infusion (circles, solid line), on the minimum mean arterial pressure (MAPmin) in normal rats.

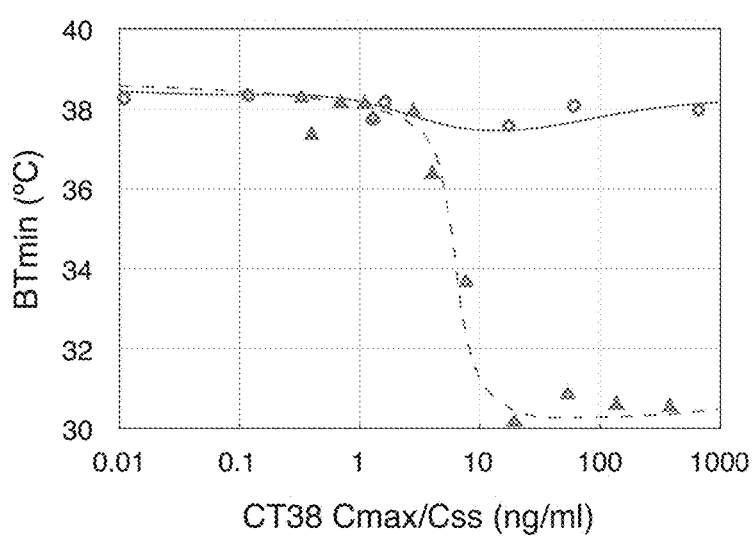

FIGURE 7C: Effect of maximum or steady state plasma concentrations (Cmax or Css) of CT38, dosed subcutaneously by bolus (triangles, dashed line) or infusion (circles, solid line), on the minimum body temperature (BTmin) in normal rats.

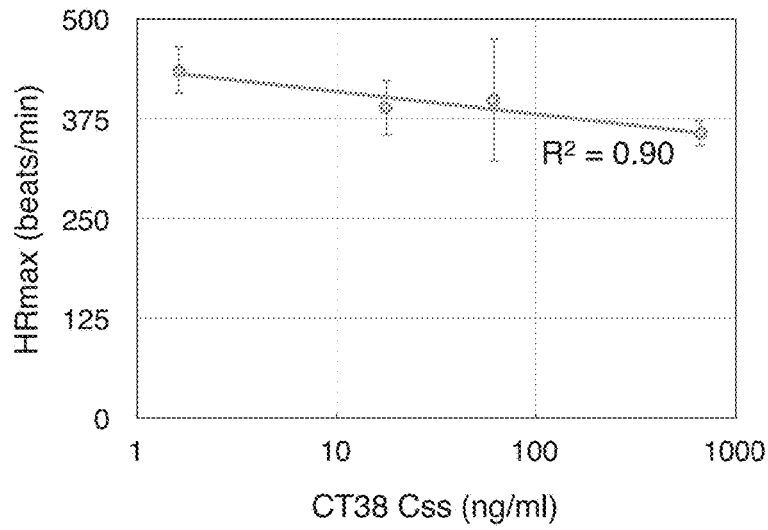
FIGURE 8A: Effect of steady state plasma concentrations (Css) of CT38, dosed subcutaneously by escalating continuous infusion, on the maximum heart rate (HRmax) in normal rats.
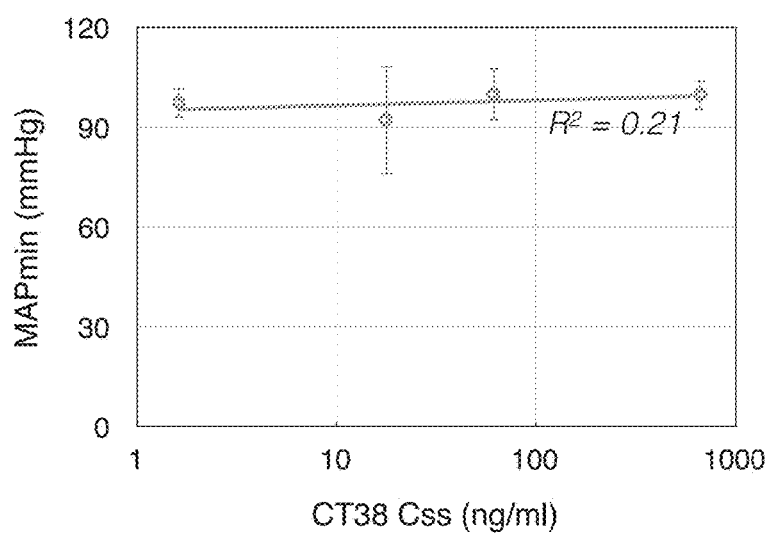
FIGURE 8B: Effect of steady state plasma concentrations (Css) of CT38, dosed subcutaneously by escalating continuous infusion, on minimum mean arterial pressure (MAPmin) in normal rats

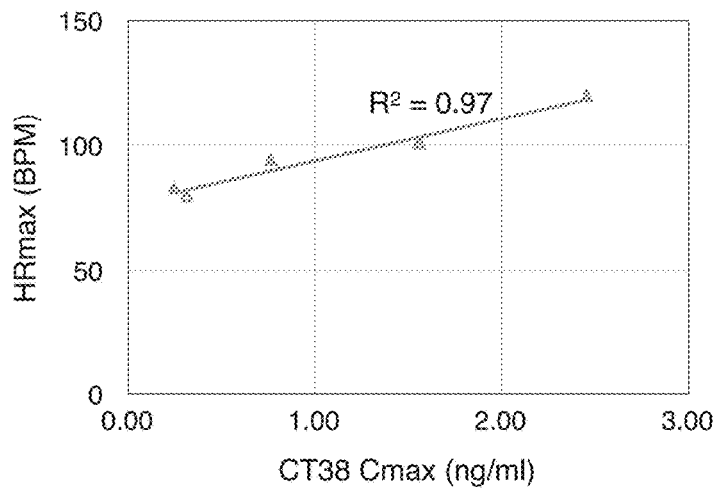

FIGURE 9A: Effect of maximum plasma concentrations (Cmax) of CT38, dosed by subcutaneous bolus, on the maximum heart rate (HRmax) in healthy human subjects.

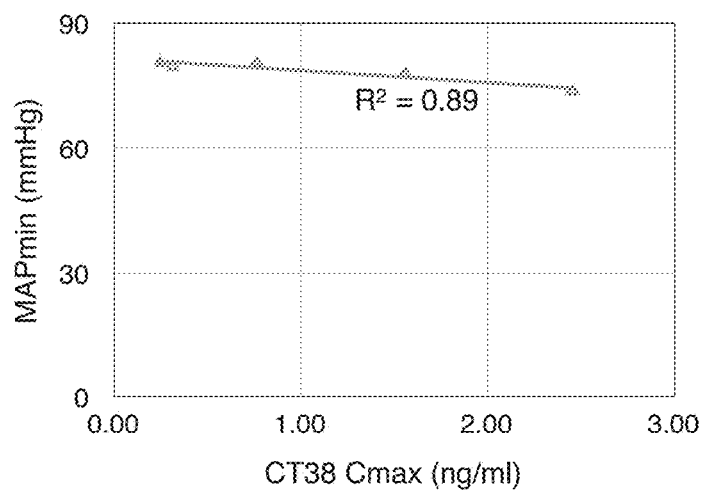

FIGURE 9B: Effect of maximum plasma concentrations (Cmax) of CT38, dosed by subcutaneous bolus, on the minimum mean arterial pressure (MAPmin) in healthy human subjects.

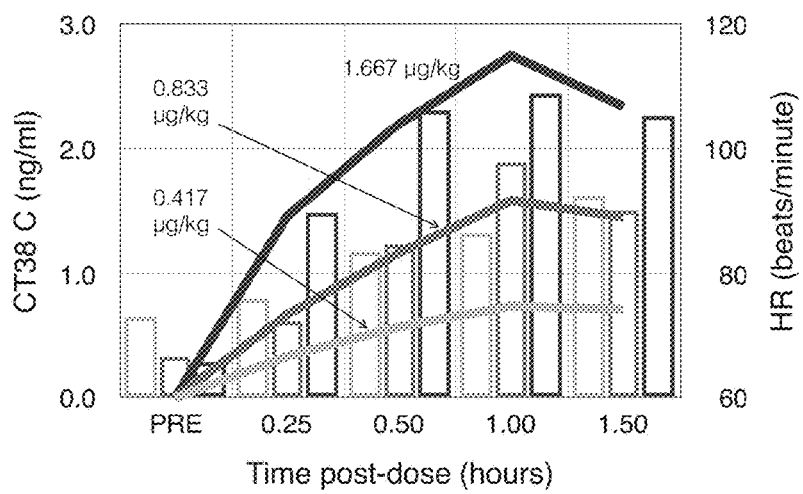

FIGURE 9C: Effects over time of plasma concentrations (C) of CT38, dosed by subcutaneous bolus, on the heart rate (HR) in healthy human subjects.

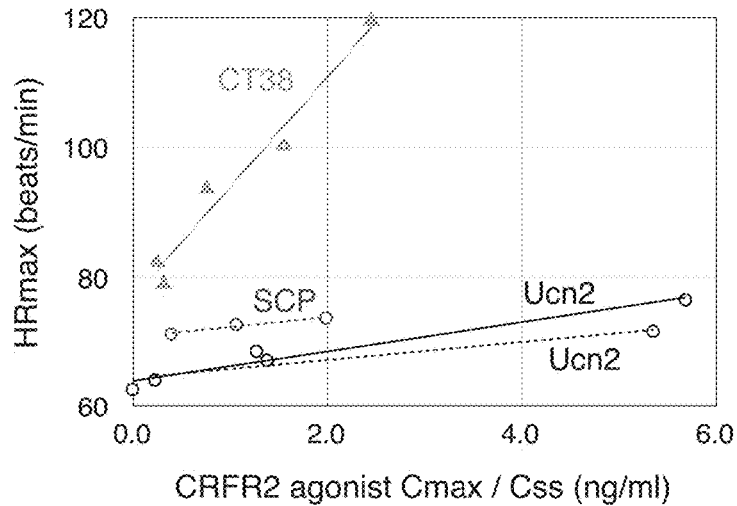

FIGURE 10: Effect of maximum or steady state plasma concentrations (Cmax or Css) of various CRFR2 agonists (CT38, SCP or Ucn2), dosed by subcutaneous bolus (triangles) or intravenous infusion (circles), on the maximum heart rate (HRmax) in healthy subjects (solid lines) or stable congestive heart failure patients (dashed lines). The table provides comparative pharmacokinetic parameters for the CRFR2 agonists.

Pharmacokinetic Parameters

|  | EC50, nmol (% of Emax) | | $t_{1/2}$ (hours) | |
| --- | --- | --- | --- | --- |
|  | CRFR1 | CRFR2 | subQ bolus | 30-min IV infusion |
| Ucn2 | > 1000 (7.6) | 4.3 (96) | 1.8 | 0.6 |
| CT38 | > 1000 (53) | 17.1 (100) | 0.9 | 0.7 |
| Ucn3 | > 1000 (10) | > 100 (60) | | |

FIGURE 11

| SEQ ID NO. | Peptide | Amino Acid Sequence |
|---|---|---|
| SEQ ID NO. 1 | CT38 | ZGPPISIDLP FQLLRKVIEI EKQEKEKQQA ANNARLLDTI-NH2 |
| SEQ ID NO. 2 | CT37 | ZGPPISIDLP FQLLRKVIEI EKQEKEKQQA ANNARLLARI-NH2 |
| SEQ ID NO. 3 | Human urocortin 1 (hUcn1) | DNPSLSIDLT FHLLRTLLEL ARTQSQRERA EQNRIIFDSV-NH2 |
| SEQ ID NO. 4 | Human urocortin 2 (hUcn2) | IVLSLDVPIG LLQILLEQAR ARAAREQATT NARILARV-NH2 |
| SEQ ID NO. 5 | Stresscopin-related peptide (SRP) | HPGSRIVLSLDVPIG LLQILLEQAR ARAAREQATT NARILARV-NH2 |
| SEQ ID NO. 6 | Human urocortin 3 (hUcn3) | FTLSLDVPTN IMNLLFNIAK AKNLRAQAAA NAHLMAQI-NH2 |
| SEQ ID NO. 7 | Strescopin (SCP) | TKFTLSLDVPTN IMNLLFNIAK AKNLRAQAAA NAHLMAQI-NH2 |
| SEQ ID NO. 8 | | ZGPPISIDLP$X_{11}X_{12}$LLRK$X_{17}$IEIEKQEK EKQQA$X_{31}X_{32}$NA$X_{35}X_{36}X_{38}X_{39}X_{40}$ wherein: $X_{11}$ is selected from F, Y, L, I, and T; $X_{12}$ is selected from Q, W, and Y; $X_{17}$ is selected from V and M; $X_{31}$ is selected from T and A; $X_{32}$ is selected from N and T; $X_{35}$ is selected from R and L; $X_{36}$ is selected from L and I; $X_{38}$ is selected from D and A; $X_{39}$ is selected from T and R; $X_{40}$ is selected from I and V |

METHODS OF TREATING DISEASES RESULTING FROM A MALADAPTED STRESS RESPONSE

CROSS-REFERENCE TO RELATED APPLICATIONS

This application is a continuation of PCT Application No. PCT/US17/57736, filed Oct. 20, 2017; which claims the benefit of U.S. Provisional Patent Application No. 62/410,764, filed Oct. 20, 2016; which are incorporated herein by reference in their entirety and to which applications we claim priority under 35 USC § 120.

SEQUENCE LISTING

The instant application contains a Sequence Listing which has been submitted in ASCII format via EFS-Web and hereby incorporated by reference in its entirety. Said ASCII copy, created on Apr. 16, 2019, is named 51049-701_301_SL.txt and is 4,644 bytes in size.

BACKGROUND

Systemic exertion intolerance disease (SEID), also known as chronic fatigue syndrome (CFS), myalgic encephalomyelitis (ME), post-viral fatigue syndrome (PVFS) or chronic fatigue immune dysfunction syndrome (CFIDS), is a chronic debilitating disease. The symptoms of SEID are wide-ranging and affect multiple body systems, for which there is clear evidence of dysfunction (e.g., in the immune and metabolic systems). However, there is no animal model of the disease, no accepted etiology, and many researchers believe that SEID represents the common endpoint of multiple etiological pathways. There are no approved therapeutics, and patients utilize therapies that provide marginal symptom relief.

SUMMARY

The present disclosure considers that SEID arises from a sufficiently intense or prolonged stress that brings about a maladaptation of the stress response, in which the corticotropin-releasing factor receptor subtype 2 (CRFR2) is up-regulated and relocated to the membranes of serotonin (5-hydroxytryptamine or 5HT) neurons in the brain. In such a configuration, a subsequent minor stress induces the response of a major stress, stimulating, rather than inhibiting, the release of 5HT in the brain. The resulting excess of 5HT plausibly explains the symptoms of SEID patients. The present disclosure proposes a treatment paradigm involving the use of a CRFR2 agonist as a therapeutic to reverse CRFR2 maladaptations, which may be curative. The present disclosure provides guidance on the form and extent of the proposed treatment.

In certain subregions of the brain, including the raphe nuclei (in the brain stem and source of 5HT in the brain) and the limbic system (i.e., hippocampus, amygdala, bed nucleus of stria terminalis or BNST, fornix, parahippocampal gyms, thalamus, hypothalamus, cingulate gyrus, ventral tegmental area, septum, periaqueductal gray, nucleus accumbens, etc.), stress can cause the up-regulation and relocation of CRFR2 to the plasma membranes of the 5HT neurons, with concomitant internalization of CRFR1 to the cytosol (see, e.g. Waselus et al. Biol Psychiatry. 66(2009):76-83 and Wood et al. Biol Psychiatry. 73(2013):1087-94). This is a normal adaptive process, but if the stress is intense or prolonged enough it can desensitize the mechanisms that would ordinarily restore homeostasis, thereby preventing the changes in CRFR2 (and CRFR1) from being restored to their basal configurations. Under subsequent stress, such maladaptations change the release of 5HT and other neurotransmitters, effectively causing the system to react to minor stress as though it were a major stress. Based upon animal models in which stress in young mice induces a persistent up-regulation of CRFR2 in the BNST of the adult mice, the present disclosure postulates that SEID is the result of such stress-induced up-regulation/relocation of CRFR2 in the previously mentioned subregions of the brain, and that these changes persist long after the triggering stress has abated (see, e.g. Victoria et al. Psychoneuroendocrinology. 38(2013):3015-28). This leads to a maladapted stress response and an inability to restore CRFR2 to the pre-disease configuration. The present disclosure describes methods of utilizing CRFR2 agonists to reverse the maladaptation and restore the pre-disease configuration.

Disclosed herein are methods for treating a functional somatic syndrome (FSS) in a human patient, the method comprising administering by controlled release a safe and effective amount of a composition comprising a CRFR2 agonist, or any analog or derivatives thereof, for a period of time during which sustained stimulation of CRFR2 in key regions of the brain, brings about CRFR2 endocytosis, which is predicted to restore normal function to a maladapted stress response. In some cases, treatment of the underlying disease with the methods described herein leads to a cure of the disease.

In some embodiments, the present disclosure provides a method for treating a functional somatic syndrome (FSS) comprising administering to a human patient in need of such treatment a safe and effective amount of a corticotropin-releasing factor receptor subtype 2 (CRFR2) agonist. In other embodiments, the administering is effective to achieve a minimum plasma concentration of the CRFR2 agonist greater than the minimum endocytotic concentration of the CRFR2 agonist in the human patient, and wherein the minimum plasma concentration is maintained over at least one treatment period. In other embodiments, the minimum plasma concentration of the CRFR2 agonist is at least about 1.1-1.9 ng/ml. In other embodiments, the minimum plasma concentration of the CRFR2 agonist is at least about 1.1-1.9 ng/ml, wherein the CRFR2 agonist is a high potency CRFR2 agonist. In other embodiments, the duration of the at least one treatment period is selected from the group consisting of about 0.5-2 hours, about 2-3 hours, about 3-4 hours, about 4-8 hours, about 8-12 hours, about 12-24 hours, and about 24-48 hours. In other embodiments, the minimum plasma concentration is maintained over two or more separate treatment periods. In other embodiments, the minimum plasma concentration is maintained over 2 to 28 separate treatment periods. In other embodiments, the separate treatment periods are separated by a period of time sufficient to ensure that the plasma concentration of the CRFR2 agonist is no longer detectable in the human patient. In other embodiments, the duration of a treatment period is adjusted in a subsequent treatment in the same patient. In other embodiments, the CRFR2 agonist is administered at a rate that does not increase the plasma concentration of the agonist in the human patient by more than a maximum rate in any 15-minute time window within any treatment period. In other embodiments, the maximum rate is no more than about 0.2 ng/ml in any 15-minute time window within any treatment period. In other embodiments, the maximum rate is no more than about 0.2 ng/ml in any 15-minute time window within any treatment period, wherein the CRFR2 agonist is a high potency CRFR2 agonist.

In some embodiments, the present disclosure provides a method for treating a functional somatic syndrome (FSS) comprising administering to a human patient in need of such treatment a safe and effective amount of a corticotropin-releasing factor receptor subtype 2 (CRFR2) agonist, wherein the administering is by controlled release. In other embodiments, the controlled release comprises a delivery methodology selected from the group consisting of subcutaneous infusion, subcutaneous depot, intravenous infusion, gastrointestinal delivery, transmucosal delivery, and transdermal patch delivery. In other embodiments, the controlled release comprises subcutaneous infusion.

In some embodiments, the present disclosure provides a method for treating a functional somatic syndrome (FSS) comprising administering to a human patient in need of such treatment a safe and effective amount of a corticotropin-releasing factor receptor subtype 2 (CRFR2) agonist, wherein the agonist is a high potency agonist. In other embodiments, the CRFR2 agonist comprises a sequence selected from the group consisting of SEQ ID NOs: 1, 2, 3, 4, 5, 6, 7, and 8. In other embodiments, the CRFR2 agonist comprises SEQ ID NO: 1.

In some embodiments, the present disclosure provides a method for treating a functional somatic syndrome (FSS) comprising administering to a human patient in need of such treatment a safe and effective amount of a corticotropin-releasing factor receptor subtype 2 (CRFR2) agonist, wherein the minimum plasma concentration, the duration of a treatment period, the number of separate treatment periods, and/or the administration rate are adjusted to account for the potency of the CRFR2 agonist being utilized. In other embodiments, the minimum plasma concentration, the duration of a treatment period, the number of separate treatment periods, and/or the administration rate are adjusted to account for the route of administration.

In some embodiments, the present disclosure provides a method for treating a functional somatic syndrome (FSS) comprising administering to a human patient in need of such treatment a safe and effective amount of a corticotropin-releasing factor receptor subtype 2 (CRFR2) agonist, wherein the duration of a treatment period, and/or the number of separate treatment periods are adjusted to account for severity of symptoms in the FSS being treated.

In some embodiments, the present disclosure provides a method for treating a functional somatic syndrome (FSS) in an adult. In other embodiments, the present disclosure provides a method for treating a functional somatic syndrome (FSS) in a child.

In some embodiments, the present disclosure provides a method for treating a functional somatic syndrome (FSS) comprising administering to a human patient in need of such treatment a safe and effective amount of a corticotropin-releasing factor receptor subtype 2 (CRFR2) agonist, wherein the FSS is systemic exertion intolerance disease (SEID). In other embodiments, the FSS is selected from the group consisting of fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), and Gulf War Illness (GWI, or Gulf War Syndrome). In other embodiments, the FSS is selected from the group consisting of non-ulcer dyspepsia, premenstrual syndrome, chronic pelvic pain, interstitial cystitis, low back pain, repetitive strain injury, atypical chest pain, non-cardiac chest pain, hyperventilation syndrome, tension headache, temporomandibular joint disorder, atypical facial pain, Globus syndrome, food hypersensitivity, and sick building syndrome. In other embodiments, the FSS is selected from the group consisting of chronic pain, anxiety, and addiction. In other embodiments, the FSS presents with the symptoms of dysautonomia. In other embodiments, the dysautonomic symptoms result from primary dysautonomia. In other embodiments, the primary dysautonomia is selected from the group consisting of postural orthostatic tachycardia syndrome, neurocardiogenic syncope, multiple system atrophy, hereditary sensory and autonomic neuropathies, and Holmes-Adie syndrome. In other embodiments, the dysautonomic symptoms result from secondary dysautonomia. In other embodiments, the secondary dysautonomia presents with the symptoms of an autoimmune disease. In other embodiments, the autoimmune disease is selected from the group consisting of systemic lupus erythematosus (lupus), multiple sclerosis, inflammatory bowel disease, rheumatoid arthritis, diabetes (type 1), celiac disease, Sjogren's syndrome, and Parkinson's disease.

In some embodiments, the present disclosure provides a method for determining the extent of a stress-induced maladaptation in a human subject, comprising: (i) measuring a physiological parameter in the human subject, wherein the physiological parameter is selected from the group consisting of heart rate, blood pressure, and body temperature; (ii) administering a certain concentration of an initial body weight adjusted bolus dose of a CRFR2 agonist and at least one or more subsequent bolus doses of the CRFR2 agonist, wherein the concentration of the CRFR2 agonist escalates in the one or more subsequent bolus doses; (iii) measuring the physiological parameter in the human subject following administration of the initial bolus dose and the one or more subsequent bolus doses; (iv) identifying the concentration of the CRFR2 agonist where a change in the physiological parameter is first measured, thereby determining a minimum stimulating bolus dose of the CRFR2 agonist to induce a change in the physiological parameter; and (v) comparing the minimum stimulating bolus dose of the CRFR2 agonist in the subject to a reference minimum stimulating bolus dose of the CRFR2 agonist for the physiological parameter, thereby determining the extent of the stress-induced maladaptation in the human subject.

In some embodiments, the present disclosure provides a method for determining the extent of a stress-induced maladaptation in a human subject comprising administering a certain concentration of an initial body weight adjusted bolus dose of a CRFR2 agonist and at least one or more subsequent bolus doses of the CRFR2 agonist, wherein the CRFR2 agonist comprises a sequence selected from the group consisting of SEQ ID NOs: 1, 2, 3, 4, 5, 6, 7, and 8. In other embodiments, the CRFR2 agonist comprises SEQ ID NO:1. In other embodiments, the initial bolus dose is a body weight adjusted bolus dose selected from the group consisting of about 0.01 µg/kg, about 0.02 µg/kg, about 0.03 µg/kg, about 0.04 µg/kg, about 0.05 µg/kg, about 0.06 µg/kg, about 0.07 µg/kg, about 0.08 µg/kg, about 0.09 µg/kg, and about 0.10 µg/kg. In other embodiments, the initial bolus dose is a body weight adjusted bolus dose of about 0.05 µg/kg. In other embodiments, the at least one or more subsequent bolus dose is a body weight adjusted bolus dose selected from the group consisting of about 0.06 µg/kg, about 0.07 µg/kg, about 0.08 µg/kg, about 0.09 µg/kg, about 0.10 µg/kg, about 0.11 µg/kg, about 0.12 µg/kg, about 0.13

µg/kg, about 0.14 µg/kg, about 0.15 µg/kg, about 0.16 µg/kg, about 0.17 µg/kg, about 0.18 µg/kg, about 0.19 µg/kg, and about 0.20 µg/kg.

In some embodiments, the present disclosure provides a method for determining the extent of a stress-induced maladaptation in a human subject, wherein the stress-induced maladaptation is a FSS. In other embodiments, the stress-induced maladaptation is systemic exertion intolerance disease (SEID). In other embodiments, the stress-induced maladaptation is selected from the group consisting of fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), and Gulf War Illness (GWI, sometimes Gulf War Syndrome). In other embodiments, the stress-induced maladaptation is selected from the group consisting of, non-ulcer dyspepsia, premenstrual syndrome, chronic pelvic pain, interstitial cystitis, low back pain, repetitive strain injury, atypical chest pain, non-cardiac chest pain, hyperventilation syndrome, tension headache, temporomandibular joint disorder, atypical facial pain, Globus syndrome, food hypersensitivity, and sick building syndrome. In other embodiments, the stress-induced maladaptation is selected from the group consisting of chronic pain, anxiety, and addiction. In other embodiments, the stress-induced maladaptation is selected from the group consisting of primary dysautonomia and secondary dysautonomia.

INCORPORATION BY REFERENCE

All publications, patents, and patent applications mentioned in this specification are herein incorporated by reference to the same extent as if each individual publication, patent, or patent application was specifically and individually indicated to be incorporated by reference in their entireties.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows the effects on maximum heart rate (FIG. 1A), minimum mean arterial blood pressure (FIG. 1B), minimum body temperature (FIG. 1C), induced by subcutaneously-administered bolus doses of a proprietary CRFR2 agonist (CT38s), in normal rats.

FIG. 2 shows the effect on respiratory rate, induced by subcutaneously-administered bolus doses of a proprietary CRFR2 agonist (CT38s), in normal rats.

FIG. 3 shows the effect on gastrointestinal transit, induced by subcutaneously-administered bolus doses of a proprietary CRFR2 agonist (CT38s), in normal rats.

FIG. 4 shows the effect on urine volume, induced by subcutaneously-administered bolus doses of a proprietary CRFR2 agonist (CT38s), in normal rats.

FIG. 5 shows the effect on norepinephrine and corticosterone secretion, induced by subcutaneously-administered bolus doses of a proprietary CRFR2 agonist (CT38), in normal rats.

FIG. 6 shows the effects on total distance traveled (FIG. 6A) and number of vertical movements (FIG. 6B), induced by subcutaneously-administered bolus doses of a proprietary CRFR2 agonist (CT38s), in normal rats.

FIG. 7 shows the effects on maximum heart rate (FIG. 7A), minimum mean arterial blood pressure (FIG. 7B) and minimum body temperature (FIG. 7C), induced by the maximum or steady state plasma concentrations (Cmax or Css) of a single dose of a proprietary CRFR2 agonist (CT38), subcutaneously-administered either by bolus (triangles, dashed lines) or by continuous infusion (circles, solid lines), in normal rats.

FIG. 8 shows the effects on maximum heart rate (FIG. 8A) and minimum mean arterial blood pressure (FIG. 8B), induced by the steady state plasma concentrations (Css) of an escalating dose of a proprietary CRFR2 agonist (CT38), subcutaneously-administered by continuous infusion (without cessation of dosing), in normal rats.

FIG. 9 shows the maximum heart rate (FIG. 9A) and minimum mean arterial blood pressure (FIG. 9B), induced by the maximum plasma concentration (Cmax) of a single ascending dose of a proprietary CRFR2 agonist (CT38), subcutaneously-administered by bolus, in healthy human subjects. FIG. 9C shows the plasma concentration of CT38 and the heart rate at specific doses of CT38 and at specific points in time.

FIG. 10 shows the effects on maximum heart rate induced by the maximum or steady state plasma concentrations of various CRFR2 agonists, including a proprietary CRFR2 agonist (CT38), urocortin 2 and stresscopin, in either healthy human subjects or stable congestive heart failure patients.

FIG. 11 shows the sequences of certain CRFR2 agonists.

DETAILED DESCRIPTION

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the appended claims define the scope of the disclosure and that methods and structures within the scope of these claims and their equivalents be covered thereby.

Unless defined otherwise, all technical and scientific terms used herein have the same meaning as is commonly understood by one of skill in the art to which this disclosure belongs. All patents and publications referred to herein are incorporated by reference.

As used in the specification and claims, the singular form "a," "an," and "the" include plural references unless the context clearly dictates otherwise.

As used herein, "treatment" or "treating" or "palliating" and "ameliorating" or "alleviating" are used interchangeably herein. These terms refer to an approach for obtaining beneficial or desired results including but not limited to therapeutic benefit. By therapeutic benefit is meant eradication or amelioration of the underlying disorder being treated. Also, a therapeutic benefit is achieved with the eradication or amelioration of at least one of the physiological symptoms associated with the underlying disorder such that an improvement is observed in the patient, notwithstanding that the patient may still be afflicted with the underlying disorder. For prophylactic benefit, treatment may be administered to a patient at risk of developing a particular disease, or to a patient reporting one or more of the physiological symptoms of a disease, even though a diagnosis of this disease may not have been made.

A "therapeutic effect", as that term is used herein, encompasses a therapeutic benefit as described above.

The term "antagonist", as used herein, includes any molecule that partially or fully blocks, inhibits, or neutralizes a biological activity of a native polypeptide disclosed herein (e.g., CRFR2). Methods for identifying antagonists of a polypeptide may comprise contacting a native polypeptide with a candidate antagonist molecule and measuring a detectable change in one or more biological activities normally associated with the native polypeptide.

The term "agonist" is used in the broadest sense and includes any molecule that mimics a biological activity of a native polypeptide disclosed herein (e.g., CRFR2). Suitable agonist molecules specifically include native polypeptides, variants of native polypeptides, peptides, small organic molecules, etc. Methods for identifying agonists of a native polypeptide may comprise contacting a native polypeptide with a candidate agonist molecule and measuring a detectable change in one or more biological activities normally associated with the native polypeptide.

The term "ligand" is used in the broadest sense and includes any molecule that binds to another molecule. For example, both agonists and antagonists of a native polypeptide (e.g., CRFR2) as disclosed herein are ligands of the native polypeptide.

"Activity" for the purposes herein refers to an action or effect of a component of a native polypeptide consistent with that of the corresponding native biologically active protein, wherein "biological activity" refers to an in vitro or in vivo biological function or effect, including but not limited to receptor binding, antagonist activity, agonist activity, or a cellular or physiologic response.

The term "high potency" as it relates to a CRFR2 agonist is used herein to mean an agonist having a half maximal effective concentration ($EC_{50}$) of 20 nM or lower in vitro.

The term "co-administration," "administered in combination with," and their grammatical equivalents, as used herein, encompasses administration of two or more agents to a human subject so that both agents and/or their metabolites are present in the subject at the same time. Co-administration includes simultaneous administration in separate composition, administration at different times in separate composition, or administration in a composition in which both agents are present.

A "safe and effective amount" means an amount of the compound (e.g., CRFR2 agonist) according to the disclosure sufficient to significantly induce a positive modification in the condition to be treated, but low enough to avoid serious side effects (such as toxicity, irritation, or allergic response) in an animal, preferably a mammal, more preferably a human subject, in need thereof, commensurate with a reasonable benefit/risk ratio when used in the manner of this disclosure. The specific "safe and effective amount" will, obviously, vary with such factors as the particular condition being treated, the physical condition of the subject, the duration of treatment, the nature of concurrent therapy (if any), the specific dosage form to be used, the specific delivery route used, the carrier employed, the solubility of the compound therein, and the dosage regimen for the composition. One skilled in the art may use the following teachings to determine a "safe and effective amount" in accordance with the present disclosure.

The term "pharmaceutically acceptable salt" refers herein to salts derived from a variety of organic and inorganic counter ions and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, "agent" or "biologically active agent" refers herein to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present disclosure.

The term "about" generally refers to a plus or minus of 1%, 2%, 3%, 4%, 5%, 6%, 7%, 8%, 9%, or 10% of the indicated value. For example, about 50% can be interpreted as between 41%-51%, 42%-53%, or 45%-55%.

As used herein, "subject" refers to an animal, such as a mammal, preferably a human.

As described herein, "controlled release" refers to a delivery methodology for administering a substance, or a therapeutic drug, over a time period. A controlled release of an agent (e.g., a CRFR2 agonist) to a mammal, including a human, includes any delivery methodology that is intended to maintain the concentration of the agent in the mammal, within a limited range, over some period of time and at a therapeutic level sufficient to achieve a given therapeutic effect. Controlled release can be continuous-release, time-release, extended-release, sustained-release, delayed-release, or prolonged-release, Controlled release is effective for maintaining or extending the dissolution, absorption, or administration of the drug to the subject to meet certain parameters for safe and effective treatment (e.g., maintaining a concentration and a duration of dosing with an agent). The substance or therapeutic drug can be a peptide, a drug, or a prodrug described herein. For example, the peptide, drug, or prodrug can be administered via controlled release using intravenous infusion, subcutaneous infusion, an implantable osmotic pump, subcutaneous depot, a transdermal patch, liposomes, subcutaneous depot injection containing a biodegradable material, or other modes of administration. In some cases, a pump is used. In some cases, polymeric materials are used. In some cases, the flow rate of the peptide, drug, or prodrug is controlled by pressure via a controlled release system or device. The controlled release system or device can be placed in proximity of the therapeutic target thus requiring a fraction of the systemic dose. In some cases, a polymer-based drug-delivery system wherein drugs are delivered from polymer or lipid systems. These systems deliver a drug by three general mechanisms: (1) diffusion of the drug species from or through the system; (2) a chemical or enzymatic reaction leading to degradation of the system, or cleavage of the drug from the system; and (3) solvent activation, either through osmosis or swelling of the system. Suitable systems are described in review articles: Langer, Robert, "Drug delivery and targeting," Nature: 392 (Supp):5-10 (1996); Kumar, Majeti N. V., "Nano and Microparticles as Controlled Drug Delivery Devices," *J. Pharm Pharmaceut Sci.* 3(2):234-258 (2000); Brannon-Peppas, "Polymers in Controlled Drug Delivery," Medical Plastics and Biomaterials, (November 1997). See also, Langer, 1990, supra; Treat et al., in *Liposomes in the Therapy of Infectious Disease and Cancer*, Lopez-Berestein and Fidler (eds.), Liss, New York, pp. 353-365 (1989); Langer, Science, 249:1527-1533 (1990). Suitable systems may include: Atrigel™ drug delivery system from Atrix Labs; DepoFoaM™ from SkyPharma; polyethylene glycol-based hydrogels from Infimed Therapeutics, Inc.; ReGel™, SQZGel™ oral, HySolv™ and ReSolv® solubilizing drug-delivery systems from MacroMed; ProGelz™ from ProGelz' Products; and ProLease™ injectable from Alkermes.

The phrases "continuous release", "sustained release", "sustain release" or "extended release" are used herein to refer to a delivery methodology for administering a substance, or a therapeutic drug, or one or more therapeutic agent(s) that is introduced into the body of a human or other mammal and continuously or continually release or infuse an amount of one or more therapeutic agents over a predetermined time period and at a therapeutic level sufficient to achieve a given therapeutic effect throughout a predetermined time period. Reference to a continuous or continual release is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrases "instantaneous release,", "bolus dose," "immediate release" are used herein to refer to a delivery methodology for administering a substance, or a therapeutic drug, or one or more therapeutic agent(s) that is introduced into the body and that is allowed to rapidly dissolve in or become absorbed at the location to which it is administered, with (unlike in the case of controlled release or continuous release) no intention of delaying, prolonging, or sustaining the dissolution, absorption, or administration of a drug. Accordingly, unlike controlled release or continuous release, bolus dose administration of a substance to a human patient would not be expected to stably maintain the concentration of the substance over a period of time (e.g., 2-3 hours).

As described herein "a biological marker," or "a biomarker" generally refers to a measurable indicator of some biological state or condition. Biological markers are often measured and evaluated to examine normal biological processes, pathogenic processes, or pharmacologic responses to a therapeutic agent or drug.

"Functional somatic syndrome" or "FSS" as used herein is meant to indicate a stress-related (or stress-induced) disease resulting from a maladapted stress response associated with a CRFR2 maladaptation (e.g., up-regulation of CRFR2) in a certain brain region or regions. Examples of a FSS include, but are not limited to, stress-related diseases such as systemic exertion intolerance disease (SEID), fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), Gulf War Illness (GWI, sometimes Gulf War Syndrome), non-ulcer dyspepsia, premenstrual syndrome, chronic pelvic pain, interstitial cystitis, low back pain, repetitive strain injury, atypical chest pain, non-cardiac chest pain, hyperventilation syndrome, tension headache, temporomandibular joint disorder, atypical facial pain, Globus syndrome, food hypersensitivity, and sick building syndrome. An overview of terms and conventional approaches to treatment for functional somatic syndromes can be found, e.g. in Henningsen et al. (Lancet 369(2007): 946-55).

"Dysautonomia" as used herein is meant to indicate a disorder of the autonomic nervous system and of its modulation by the 5HT and/or CRF systems. Dysautonomia is generally characterized by a heart rate variability, high resting heart rate, inability to alter heart rate with exercise, and exercise intolerance, orthostatic intolerance/hypotension, thermoregulatory intolerance, digestive or urinary abnormalities. Primary dysautonomia is generally considered to be caused by either genetic factors or degenerative neurologic diseases while secondary dysautonomia may occur due to injury or de-regulation of the autonomic nervous system from an acquired disorder.

Subject

Regulation or treatment of a functional somatic syndrome (FSS) can benefit a variety of subjects. The subject can be a mammal. In a preferred embodiment, the subject can be a human. In some embodiments, the subject is an adult. In other embodiments, the subject is a child.

Overview

The application relates to compositions, methods and kits that relate to treating a FSS by administering to a human subject in need thereof a safe and effective amount of a CRFR2 agonist to effect sustained CRFR2 stimulation over a treatment period. In some embodiments, the FSS is systemic exertion intolerance disease (SEID). In other embodiments, the FSS is fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), Gulf War Illness (GWI, sometimes Gulf War Syndrome).

Systemic Exertion Intolerance Disease

SEID is a complex, multi-symptom disorder, which usually has a sudden onset, and is often triggered by infection or other stress including but not limited to immunization, anesthetics, physical trauma, environmental chemicals, and blood transfusions (see, e.g., Committee on the Diagnostic Criteria for Myalgic Encephalomyelitis/Chronic Fatigue Syndrome. Washington (DC): National Academies Press (US); 2015 February) Its hallmark is a profound physical and mental fatigue that worsens with activity (referred to as post-exertional malaise or PEM), is not improved by sleep, and can persist for years with most patients never regaining their pre-disease level of health or functioning. Currently, there are no approved therapeutics for SEID. Patients are unable to handle the activities of daily living, and experience a quality of life worse than that of other chronic diseases, such as cancer, multiple sclerosis, diabetes or depression.

SEID patients may present with a variety of subsystem abnormalities. These include: (i) altered hypothalamic-pituitary-adrenal (HPA) axis response, for example, less responsive to a challenge, altered circadian rhythm, increased glucocorticoid negative feedback, and reduced levels of corticotropin-releasing factor (CRF), adrenocorticotropic hormone (ACTH) and cortisol; (ii) immune system dysfunction, for example, a persistent flu-like state, prone to infection, alterations in acute phase proteins, cytokines, chemokines and immune cells, with the degree of dysfunction correlated with disease severity and duration; (iii) metabolic abnormalities, for example, mitochondrial dysfunction from either lack of substrate or chemical inhibition, abdominal obesity, high triglycerides, elevated fasting glucose, decreased high-density lipids, prone to Metabolic Syndrome; (iv) sympathetic nervous system dysfunction, for example, increased norepinephrine and/or norepinephrine receptor sensitivity, abnormal interactions with HPA and hypothalamic-pituitary-thyroid axes; and (v) abnormalities of the 5HT system, for example, increased 5HT and/or $5HT_{1A}$ autoantibodies, decreased 5HT receptor expression and/or decreased $5HT_{1A}$ binding potential.

SEID patients may also show evidence of oxidative and nitrosative stress, reduced cortical blood flow, orthostatic intolerance, high resting heart rate, thermostatic instability, muscle pain and weakness, sleep disruption, cognitive impairments such as poor memory, slow information processing and attention deficit, atypical depression, and anatomical derangements of the brain. These symptoms may worsen with activity (i.e., PEM) with patients experiencing exercise-induced exacerbations of pain, weakness, nausea, sensation, cognition, depression/anxiety, and sleep, many of which have been implicated in worsening fatigue.

While the etiology of SEID is unknown, the diversity of triggers suggests an upstream cause, and the considerable overlap between the symptoms of SEID and those of chronic stress suggests the involvement of the stress response and the HPA axis. Risk factors such as early life stress, childhood adversity/trauma, and cumulative life stress, and the fact that life stress in the period immediately prior to the onset of SEID increases susceptibility to known triggers, all support the notion of stress system involvement. However, most patients do not show any overt stress system dysfunction until after the initiating trigger, suggesting that if the stress response is involved, the initiating trigger might have adapted the stress response in a manner that persists post-trigger (more so because stress provokes brain adaptation throughout life). Furthermore, susceptibility to SEID is influenced by personality (correlated with neuroticism, unhealthy perfectionism and introversion), and symptom severity is affected by coping styles (particularly escape-avoidance) and stress management skills. The behavioral nature of these influences, together with the fact that cognitive behavioral therapy can improve symptoms, suggests that if a maladapted stress response is causal in SEID, then the likely locus of such a maladaptation is in the components of the system that influence the behavioral response to stress.

The behavioral response to stress is mediated largely by the interaction between the corticotropin-releasing factor (CRF) system and the serotonin (5HT) system within the brain.

CRF System

CRF and its related peptides, urocortin(s) 1, 2 and 3 (Ucn1, Ucn2 and Ucn3) mediate the stress response via two receptors: CRFR1 (widely distributed in the brain) and CRFR2 (restricted to subcortical areas). CRF is selective for both CRFR1 and CRFR2, but preferentially selective for CRFR1; Ucn1 is equally selective for CRFR1 and CRFR2; and Ucn2 and Ucn3 are CRFR2-selective. Ucn1 and Ucn2 exhibit high binding affinity for CRFR2. In some cases, CRF is referred to as corticotropin-releasing hormone (CRH). CRFR[1/2] can also be referred to as $CRF_{[1/2]}$, CRF [1/2]R, CRF-R[1/2], CRF-[1/2]R, CRHR[1/2], $CRH_{[1/2]}$, CRH[1/2] R, CRH-R1/2, CRH-[1/2]R.

Serotonin System

Serotonin (5HT) in the brain is released from the raphe nuclei in the brain stem, via 5HT neurons that extend throughout the limbic system (hippocampus, amygdala, bed nucleus of stria terminalis or BNST, fornix, parahippocampal gyrus, thalamus, hypothalamus, cingulate gyrus, ventral tegmental area, septum, periaqueductal gray, nucleus accumbens) and cortex. These 5HT neurons are topographically organized with region- and subregion-specificity of both receptor expression as well as co-localization with other neurons, which together release a variety of neurotransmitters/neuropeptides (e.g., CRF, Ucn1, gamma-aminobutyric acid or GABA, dopamine, norepinephrine, glutamate, acetylcholine, histamine) throughout the brain. The release of 5HT acts via receptors (14 subtypes grouped into 7 families) expressed throughout the brain in a receptor subtype-specific fashion (often with individual neurons expressing multiple receptor subtypes), to regulate behavior (e.g., mood, perception, reward, anger, aggression, attention, appetite, memory, sexuality) and physiology (e.g., pain sensation, bone mass, tissue regeneration, platelet coagulation, gastrointestinal function).

CRF-5HT Interaction

Stress triggers the release of CRF from the paraventricular nucleus of the hypothalamus, adrenocorticotropic hormone from the pituitary, cortisol and epinephrine from the adrenal glands (i.e., the HPA axis), and norepinephrine from the locus coeruleus. Cortisol primes the system to cope with the perceived stress, promoting a response that is pro-inflammatory in case of injury, insulin resistant to provide glucose, and inhibitory of non-essential function such as the hypothalamic-pituitary-thyroid and hypothalamic-pituitary-gonadal axes.

Stress also activates the 5HT system. Animal models show that low stress, releasing low levels of CRF in the raphe nuclei, predominately activates CRFR1, which is present in the membranes of GABA neurons in the basal state, and this increases the release of GABA. Since GABA tonically inhibits 5HT, the increased release of GABA decreases the release of 5HT in the downstream targets, for example, in the limbic system and cortex. In contrast, high stress, releasing high levels of CRF in the raphe nuclei, brings about an acute adjustment, whereby CRFR1 internalizes, and CRFR2 is both up-regulated and relocated to the membranes of 5HT neurons, where its activation increases the release of 5HT. The release of 5HT from the raphe nuclei under stress reaches all parts of the limbic system and the cortex and is fundamental to modulating the behavioral stress response. Within the limbic system many of the individual structures (e.g., the hippocampus, amygdala, BNST, hypothalamus, periaqueductal gray, nucleus accumbens) show a co-localization of CRFR1, CRFR2 and 5HT neurons, and undergo similar stress-induced adaptations involving CRFR1 and CRFR2 expressions, as in the raphe nuclei. Note also that while CRFR1 and CRFR2 do localize within these structures, they tend not to overlap. CRFR1 and CRFR2 may be expressed in different regions of the same structure. This configuration allows for precise modulation of 5HT and other neurotransmitters/neuropeptides in response to stress.

The release of 5HT in this manner mediates excitatory and inhibitory neurotransmission, to modulate the immune response, and to regulate metabolism and energy balance, influencing circulating levels of insulin, ghrelin and leptin. 5HT in the amygdala and/or periaqueductal gray and descending 5HT in dorsal horn neurons can be associated with pain modulation or perception. 5HT in the hypothalamus controls thermoregulation. 5HT along with norepinephrine can promote wakefulness. Stress management techniques can reduce the release of 5HT under stress.

At stress cessation, elevation of the key stress mediators are reversed to restore homeostasis. Cortisol levels are reduced by glucocorticoid negative feedback in the hippocampus and prefrontal cortex, while cortisol-induced expressions of Ucn2 and Ucn3 in the periphery restore homeostasis of the immune system (by down-regulating acute phase proteins, cytokines, chemokines and immune cells), and the metabolic system (by modulating insulin/ glucagon and muscle calcium). Within the brain, inhibitory $5HT_{1A}$ autoreceptors reverse elevations of 5HT, while Ucn1 is thought to reverse the effects of CRFR1 and CRFR2 stimulation (e.g., on the hypothalamic-pituitary-gonad and hypothalamic-pituitary-thyroid axes, norepinephrine release), and bring about CRFR2 endocytosis on 5HT neurons.

Maladaptation of the Stress Response

Animal models show that under intense or prolonged sub-threshold stress, and particularly early life stress, the restorative mechanisms can become desensitized, and the acute changes in CRFR2 within the raphe nuclei and their downstream targets can persist long after stress cessation. Without being bound to any theory, a stress that is sufficiently intense or prolonged to cause CRFR2 up-regulation and relocation to the membranes of 5HT neurons in the raphe nuclei and/or their target regions, possibly concomitant with the desensitization of inhibitory $5HT_{1A}$ autoreceptors, can disrupt the return to pre-stress homeostasis, leaving CRFR2 in the membranes of the 5HT neurons. Under such a maladaptation, subsequent low-level stress, releasing dually-selective CRF in the raphe nuclei that would ordinarily stimulate CRFR1 and inhibit 5HT release, instead stimulates CRFR2 and increases 5HT release, effectively converting a minor stress into a major stress and increasing the downstream stress response and cortisol release. In this manner, the stress system becomes dysfunctional with respect to the release of 5HT under subsequent stress.

Thus, the present disclosure considers that SEID results from an exposure to a stressor/trigger, of sufficient intensity or duration, that up-regulates/relocates CRFR2 to the plasma membrane of neurons in the raphe nuclei and/or their downstream targets, likely concomitant with CRFR1 internalization, which inhibits the restoration of homeostasis and leaves a maladapted stress response that affects the release of 5HT and other neurotransmitters under subsequent stress.

CRFR2 and CRFR1 maladaptations, thereby causing an increased and/or prolonged release of brain 5HT even under minor stress, explain virtually all SEID pathology including anomalies of the 5HT system, the HPA axis and norepinephrine, the immune system and the metabolic system. Increased brain 5HT has been implicated in orthostatic intolerance (influenced by the hypothalamus, limbic system and raphe nuclei), a high resting heart rate and heart rate variability (influenced by CRFR2 in the BNST), thermoregulatory intolerance (controlled by 5HT in the hypothalamus), cognitive dysfunction (seen in Alzheimer's patients at the stage of amnesic mild cognitive impairment), sleep disruption (5HT along with norepinephrine promotes wakefulness), pain (5HT in the amygdala and/or periaqueductal gray and descending 5HT in dorsal horn neurons), muscle weakness (insulin-resistant implications of prolonged stress and extended periods of inactivity), fatigue (excess 5HT inhibits motor neuron excitation), and PEM (exercise induces an increase in brain 5HT). An excess of brain 5HT also explains other characteristics of SEID including the variety of triggers (since all provoke the HPA axis and would thus be affected by maladaptations within the raphe nuclei, limbic system and/or cortex), familial association (which may be partially genetic or due to similar stress exposure), gender bias (since, relative to males, females may have a heightened stress response mostly through CRFR1- and CRFR2-related mechanisms), early life stress as a risk factor (i.e., when the brain is at its most adaptable), estrus-related symptom worsening (which may be associated with estradiol up-regulating CRFR2 in the raphe nuclei), positive effects of cognitive behavioral therapy (since stress management techniques reduce the stress response), patient-to-patient variability (which is related to personality, coping style and individual stress history), and the occurrence of good days (low stress) and bad days (high stress).

SEID patients may exhibit many of the key symptoms of dysautonomia, including heart rate variability, high resting heart rate, inability to alter heart rate with exercise and exercise intolerance, orthostatic intolerance/hypotension, thermoregulatory intolerance, digestive or urinary abnormalities. Primary dysautonomia is generally considered to be caused by either genetic factors or degenerative neurologic diseases while secondary dysautonomia may occur due to injury or de-regulation of the autonomic nervous system from an acquired disorder. The present disclosure ascribes the dysautonomia in SEID to an excess of 5HT within the limbic system during stress, which may have resulted from CRFR2 maladaptations in the raphe nuclei, limbic system and/or cortex, rather than damage to the autonomic system per se. This would also explain why dysautonomic symptoms in SEID patients can vary considerably, both inter- and intra-patient.

Therapeutic Approach

In one aspect, the present disclosure is related to the idea that SEID results from CRFR2/CRFR1-5HT maladaptations, and that it would be advantageous to modulate the effects of 5HT and/or CRFR2 on the stress response. Among the options for doing so are blocking 5HT via a 5HT antagonist, blocking the endogenous ligands that bind to CRFR2 in the brain (i.e., CRF and Ucn1) via CRF/Ucn1 antibodies, or blocking aberrant expressions of CRFR2 via CRFR2 antagonists. These approaches are problematic for a number of reasons. They would effectively block the stress response, which may cause the patient to be exposed to additional health risks. They would have to be administered chronically, and in a manner that acted centrally and specifically not peripherally. Such approaches may be non-specific and may cause numerous side effects given the distribution of CRFR1, CRFR2, and 5HT receptors both centrally and peripherally. Moreover, blocking 5HT would be impractical given the many receptor subtypes and the vast number of functions that 5HT mediates. Antibodies for CRF/Ucn1 are equally impractical as these would effectively prevent both CRFR2 and/or CRFR1 stimulation and so block the stress response. Disclosed herein are methods, compositions, and kits for treating a FSS by reversing the maladapted expressions of CRFR2.

In one aspect, the present disclosure relates to using CRFR2 agonists to bring about a persistent receptor desensitization or endocytosis (internalization), in SEID, where a postulated up-regulation of CRFR2 in key regions of the brain gives rise to a maladapted stress response. As with most G-protein coupled receptors (GPCRs), CRFR2 is susceptible to intracellular mechanisms that rapidly attenuate signaling output and prevent cell overstimulation. Such desensitization involves phosphorylation by GPCR kinases, and transient recruitment of β-arrestin2 (β-arrestin1 to a lesser degree) and clathrin to the plasma membrane, followed by rapid endocytosis. Agonists have been shown to bring about endocytosis of CRFR2a and CRFR2β relatively quickly (15 minutes in vitro) in a manner dependent upon time and agonist potency, and specifically not via low-potency CRF. Thus, in another aspect the present disclosure relates to the idea that in diseases postulated to result from stress-induced CRFR2 up-regulation/relocation in critical brain regions, bringing about some level of CRFR2 endocytosis, in essence reversing prior stress maladaptations, might provide symptomatic relief and might even restore the original receptor configuration in these brain regions, which would be curative.

The notion of using a CRFR2 agonist to treat diseases in which CRFR2 may be up-regulated is counter-intuitive as it would be expected to worsen symptoms. Examples 1, 2, 3 and 4 respectively show that a bolus dose of a proprietary CRFR2-selective agonist, CT38s, in normal rats, transiently induced the major symptoms of dysautonomia such as changes in heart rate, blood pressure, temperature, respiratory rate, gastrointestinal transit time and renal function, all present to varying degrees in SEID. Example 5 shows that a bolus dose of CT38 in normal rats also transiently increased the stress response, releasing cortisol and norepinephrine (which is elevated in SEID patients). Example 6 shows that a bolus of CT38s caused a major reduction in spontaneous motor activity which is evaluated by total distance traveled and number of vertical movements, a proxy for the fatigue of SEID. Example 9 shows that a bolus dose of CT38s, in heathy human subjects, transiently increased heart rate and decreased blood pressure. Finally, over-expression of Ucn3, an endogenous CRFR2-selective agonist, has been shown to induce anxiety and attenuate the HPA axis and stress response, in mice.

It is noteworthy, that a bolus dose of a CRFR2 agonist, essentially mimicking the effects of high stress, or low stress on a background of CRFR2 up-regulation, induces the major symptoms of SEID, which is consistent with the involvement of CRFR signaling in SEID.

Implications of Therapeutic Approach

The foregoing has important implications for treatment. First, neither 5HT release nor CRFR2 expression can be measured in a live brain undergoing stress, much less so at the level of the individual components or even neurons of the raphe nuclei, limbic system and cortex. Not only does this provide a plausible explanation for the failure of prior research to identify the etiology of SEID, it suggests the implausibility of a causal diagnostic biomarker(s) in humans. Thus, the diagnosis of SEID will likely remain a diagnosis of exclusion.

Second, the degree of dysfunction in a given SEID patient will be related to the level of CRFR2 up-regulation within the raphe nuclei, limbic system and cortex. For instance, SEID patients often exhibit a high resting heart rate, which has been shown to correlate with symptom severity. The heart rate under stress (but not the tonic regulation) is modulated by the BNST, and therefore directly related to the level of CRFR2 up-regulation, in the BNST. Accordingly, in one aspect the present disclosure relates to the idea that relative to a SEID patient with mild symptoms, a SEID patient with severe symptoms and a high resting heart rate, will be more sensitive to the effects of a CRFR2 agonist, which may result in experiencing a sharper rise in heart rate, and will require more endocytosis to reverse CRFR2 up-regulation, and consequently more sustained CRFR2 stimulation. In some embodiments, both the initial dose, as well as the duration of treatment will be patient-specific. Described below are methods for gauging both the extent of patient dysfunction and the patient-specific therapeutic dose.

Third, in the absence of measurable biomarkers, any level of therapeutic effect (including cure of the subject disorder) can only be measured indirectly, via global scales or individual symptom metrics, where an improvement of 20% or more is generally considered clinically meaningful. Examples of global scales include but are not limited to the Fatigue Severity Scale, Multidimensional Fatigue Inventory (MFI-20), Patient Global Impression of Change scale (PGIC), Clinical Global Impression of Change scale (CGIC), Karnofsky Performance Scale, Fibromyalgia Impact Questionnaire (FIQ), Short Form-36 (SF-36), Mental Health Inventory (MHI), Clinical-Administered PTSD (CAPS), Inventory of Depression Symptomology (IDS(C)), Hamilton Depression Scale (HAMD-17), Activities of Daily Living Index, visits to the hospital/emergency room, and many others. In addition there are numerous individual symptom scales for fatigue/exercise intolerance (cardiopulmonary exercise testing via stationary bicycle, Modified Fatigue Impact Scale), pain (visual analog scale), sleep (Pittsburgh Sleep Quality Index, American Academy of Sleep Medicine-approved scales for sleep satisfaction quality and improved daytime functioning), cognitive dysfunction (Perceived Deficits Questionnaire, Short Check List-90 Revised), orthostatic intolerance (tilt-table test), blood tests (measuring levels of cortisol, norepinephrine, immune/metabolic system markers, etc.), changes in vitals (i.e., heart rate, blood pressure, body temperature, respiratory rate), use of concomitant medication. The foregoing are not intended to be an exhaustive list of possible metrics for assessing clinical improvement in a FSS, including SEID. Indeed virtually any clinically-validated instrument addressing one or more symptoms of the FSS, including SEID, can be utilized. A cure of a FSS, such as SEID, would mean observing a clinically meaningful improvement in one or more global scales or in one or more individual symptom metrics in a given patient following treatment, coupled with a normalization of more complex behaviors (e.g., resumption of regular work schedule), maintained for at least 6 months after treatment.

Therapeutic Intervention

One aspect of the present disclosure involves a dosing regimen, in which sustained stimulation via a controlled release of a suitably potent CRFR2 agonist, will induce persistent CRFR2 endocytosis in the raphe nuclei, limbic system and cortex, and bring about long-lasting symptom improvement in SEID. In Examples 7 and 8, a continuous infusion of CT38 was able to desensitize heart rate effects. Since high stress acts via CRFR2, and since the heart rate under stress is mediated by CRFR2 in the BNST, the loss of heart rate effect through sustained CRFR2 stimulation most likely resulted from CRFR2 endocytosis in the BNST that persisted (but not in the cardiovascular system, where CRFR2-controlled blood pressure only partially desensitized). Furthermore, since the BNST is one of several subregions in the brain (including the raphe nuclei, limbic system and cortex) that are thought to undergo similar, stress-induced maladaptations involving CRFR2 up-regulation/relocation, it is reasonable to expect that sustained stimulation of CRFR2 via a CRFR2 agonist will bring about a persistent CRFR2 endocytosis in these other subregions of the brain (where CRFR2 up-regulation and subsequent endocytosis is part of the normal adaptive process). This is further supported by Example 8, which showed no evidence of CRFR2 resensitization, despite continuous stimulation over 15 days. For example, a controlled release of CT38s, a potent CRFR2-selective agonist ($EC_{50}$ 17.1 nmol achieves maximal CRFR2 stimulation, see Example 10), in a human patient with SEID, dosed at a level to induce a plasma concentration of at least 1.1-1.9 ng/ml (see Example 7) by subcutaneous infusion, is projected to bring about CRFR2 endocytosis within the raphe nuclei and/or limbic system that persists following cessation of dosing, thereby resulting in long-lasting symptom improvement.

The concept of receptor endocytosis as a treatment has been utilized via agonists that induce a transient endocytosis of the gonadotropin-releasing hormone receptor, thereby preventing the release of luteinizing hormone and follicle-stimulating hormone, which play a role in the progression of steroid-dependent conditions (e.g., endometriosis, leiomyomas, infertility, breast cancer or prostate cancer). Long-acting agonists are required to maintain this endocytosis. In contrast, CRFR2 in the raphe nuclei, limbic system and cortex is intended to adapt, and thus it is predicted that any achieved CRFR2 endocytosis will persist. Accordingly, in one aspect of the present disclosure, a limited number of treatments with a CRFR2 agonist may be sufficient to induce long-lasting symptom reduction in a FSS, such as SEID.

The controlled release dose to achieve sustained CRFR2 stimulation, thereby causing receptor endocytosis, is determined by 4 main factors: (i) CRFR2 agonist potency; (ii) the dose must achieve and maintain a plasma concentration at or above the minimum endocytotic concentration (~1.1-1.9 ng/ml of CT38 in healthy humans, see Example 7); (iii) the minimum endocytotic concentration must be maintained over a period of ~2-3 hours (based on at least 15 minutes in vitro); and (iv) the rate of dosing must not be so high as to induce plasma concentrations associated with side effects by bolus dosing (i.e., not greater than ~0.2 ng/ml of CT38 in any 15-minute period in healthy humans, see FIG. 9C). However, as noted above, both the side effect-inducing dose and the ultimate level of endocytosis required for therapeutic effect will depend upon the extent to which CRFR2 is up-regulated in a given patient at the onset of treatment. These constraints define a dosing paradigm whereby the greater the symptom severity, the lower will be the initial controlled release dose level to be administered, but the longer the controlled release dose will have to be maintained to achieve therapeutic effect.

Accordingly, the dose of CRFR2 agonist needed to treat the FSS as described herein can vary between individual patients suffering from different degrees of severity of a disease.

In general, in humans, a potent CRFR2 agonist such as CT38, administered in a manner to induce relatively low plasma concentrations (~1.1-1.9 ng/ml and below), regardless of the duration of dosing, would be expected to increase heart rate and decrease blood pressure and body temperature (very slightly), with no evidence of receptor desensitization or endocytosis. Relatively high plasma concentrations (~3.2 ng/ml and above), regardless of the duration of dosing, would be expected to partially reverse the effects seen at low plasma levels, i.e., a loss of or reduction in the ability to induce an increase in heart rate or a decrease in blood pressure and body temperature, suggesting receptor desensitization or endocytosis.

However, treatment using high concentrations of a potent CRFR2 agonist would be impractical for fear of inducing undesirable side-effects. In contrast, for relatively intermediate plasma levels (above ~1.1-1.9 ng/ml and below ~3.2 ng/ml), the period of time during which such intermediate concentration is maintained, determines the induced effects on heart rate, blood pressure and body temperature. Specifically, where a potent CRFR2 agonist such as CT38 ($EC_{50}$ 17.1 nmol) or Ucn2 ($EC_{50}$ 4.3 nmol) is administered in a manner to induce such intermediate plasma concentrations, instantaneous (bolus) dosing would be expected to increase heart rate and decrease blood pressure and body temperature, while continuous dosing (infusion) would be expected to result in a loss of the ability to induce an increase in heart rate, a decrease in blood pressure, or a decrease in body temperature. Accordingly, beyond a threshold intermediate plasma concentration, sustained, but not transient, stimulation of CRFR2 would be expected to cause receptor desensitization or endocytosis. The present disclosure relates to methods of treating a FSS, such as SEID, by controlled release dosing of a CRFR2 agonist at a level selected to maintain plasma concentrations within the intermediate range (precisely defined by the specific agonist potency and pharmacokinetics) for at least one treatment period and over a limited number of dosing periods.

Accordingly, in certain embodiments, the present invention relates to administering a CRFR2 agonist to a subject having a FSS, at a dose level sufficient to ensure plasma concentrations of the CRFR2 agonist above the threshold for endocytosis (i.e., above about 1.1-1.9 ng/ml for a high potency CRFR2 agonist), maintained for a period of time long enough to ensure CRFR2 endocytosis in key brain regions (e.g., raphe nuclei, limbic system, cortex), as measured by symptom or global improvement. In some embodiments, a single treatment period with a CRFR2 agonist is utilized, such that the treatment period comprises sustained stimulation of CRFR2 lasting about 0.5-2 hours, about 2-3 hours, about 3-4 hours, about 4-8 hours, about 8-12 hours, about 12-24 hours, or about 24-48 hours. In other embodiments, 2 to 28 separate treatments with a CRFR2 agonist are utilized, such that each treatment period comprising sustained stimulation of CRFR2 lasting about 0.5-2 hours, about 2-3 hours, about 3-4 hours, about 4-8 hours, about 8-12 hours, about 12-24 hours, or about 24-48 hours. In one embodiment, a CRFR2 agonist is administered to a subject having a FSS, by controlled release (e.g., subcutaneous infusion) for a treatment period lasting about 0.5-2 hours, about 2-3 hours, about 3-4 hours, about 4-8 hours, about 8-12 hours, about 12-24 hours, or about 24-48 hours, over one to 28 separate treatment periods.

In another aspect of this invention, it will be readily apparent to those skilled in the art, that the plasma concentrations at which sustained stimulation of the receptor brings about desensitization and endocytosis, will depend not only on the potency of the CRFR2 agonist, but also the dose level and route of administration, which will alter the plasma concentration of the CRFR2 agonist at the receptor. Given knowledge of the specific CRFR2 agonist potency, and the pharmacokinetics for the route of administration dosing models can be constructed to achieve the target plasma concentration. Exemplary information on routes of administration, dosing models, and methods of computation can be found in: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999). In another embodiment, the controlled release comprises a continuous delivery methodology selected from the group consisting of subcutaneous infusion, intravenous infusion, gastrointestinal delivery, transmucosal delivery and transdermal patch delivery.

Another aspect of the disclosure incorporates the method to gauge the level of dysfunction in a given patient suffering from a FSS, such as SEID, in order to estimate the plasma concentration of the CRFR2 agonist needed for treating the patient, for a given route of administration. SEID patients can exhibit a high resting heart rate that is correlated with symptom severity, which is consistent with CRFR2 up-regulation/relocation in the BNST. A high resting heart rate is not appropriate as a diagnostic across a population, as heart rate is affected by other variables such as age, gender, weight, lifestyle. However, in one embodiment of the present invention, heart rate is utilized as a crude diagnostic in a given patient (i.e., intra-patient), as a marker for the extent of prior stress-induced maladaptation. For example, for a given CRFR2 agonist, the minimum stimulating bolus dose required to provoke an increase in the heart rate should be lower in a SEID patient than in a normal subject (because of a relative up-regulation of CRFR2 in the BNST). The lower the minimum stimulating bolus dose of the $CRFR_2$ agonist, the more CRFR2 is up-regulated in critical brain subregions, and the greater is the level of dysfunction in that patient. In another embodiment, the minimum stimulating bolus dose of the CRFR2 agonist is determined by escalation, starting at a very low bolus dose (e.g., 0.05 µg/kg of body weight of CT38s in humans by subcutaneous injection), and (following suitable washout) increasing this to the point where an increase in the heart rate is first noted. This minimum stimulating bolus dose of the CRFR2 agonist to induce a heart rate increase is a measure of the level of dysfunction in a given patient and can be compared to the minimum stimulating bolus dose in healthy young males (e.g., 0.2 µg/kg of body weight of CT38s, see Example 9). In some embodiments, the level of dysfunction in a given patient suffering from a FSS is gauged prior to beginning treatment with a controlled release of a CRFR2 agonist. In other embodiments, the minimum stimulating bolus dose determined as described is used as the starting dose for controlled release of a CRFR2 agonist.

Another aspect of the disclosure incorporates a preliminary capability to determine when to cease treatment in a given patient. For example, the initially-determined minimum stimulating bolus dose of a CRFR2 agonist to induce a heart rate increase in a given patient should increase following treatment as described above. When the minimum stimulating bolus dose for the SEID patient approximates that of healthy subjects (e.g., 0.2 µg/kg of body weight of CT38s in healthy young males, see Example 9), CRFR2 is no longer up-regulated in the BNST. Accordingly, in some embodiments, the minimum stimulating bolus dose of a CRFR2 agonist to induce a heart rate increase is measured in the patient following a treatment period comprising controlled release dosing with a CRFR2 agonist. In some embodiments, treatment is stopped when the minimum stimulating bolus dose for the patient approximates that of healthy subjects. Note that since it is possible for CRFR2 to remain up-regulated in other regions of the brain, which do not affect the heart rate, it may still be appropriate to continue treatment, even after the heart rate suggests a return of CRFR2 expression to basal levels in the BNST.

In another embodiment of the present invention, recognizing that SEID patients often exhibit orthostatic intolerance (related to low blood pressure), involves the notion that blood pressure can be used in much the same way as heart rate, both as a method to determine the level of dysfunction in a given SEID patient, as well as a method to determine when to cease treatment in that patient.

Another aspect of this disclosure, recognizing that SEID patients can exhibit thermostatic intolerance often with low body temperature, involves the notion that body temperature can be used in much the same way as heart rate, both as a method to determine the level of dysfunction in a given SEID patient, as well as a method to determine when to cease treatment in that patient. Specifically, for example, a controlled release of CT38s, delivered by subcutaneous infusion in a human patient with SEID, that achieves and maintains a plasma concentration of at least 1.1-1.9 ng/ml for at least 2 hours, is projected to bring about some endocytosis within the limbic system, thereby resulting in measurable improvements in heart rate, blood pressure and body temperature abnormalities.

For practical purposes, the human dosing range of CT38s (or similarly potent CRFR2 agonists) by subcutaneous infusion is expected to have a lower limit of ~3-9 µg/kg/day necessary to bring about endocytosis (i.e., 1-3 ng/ml in rats, equivalent to an infusion of ~18-54 µg/kg/day in rats, or, by allometry ~3-9 µg/kg/day in humans). In one embodiment, some endocytosis can be achieved at a single human dose level of ~0.9 µg/kg of CT38s (or similarly potent CRFR2 agonists) delivered by subcutaneous infusion over a period of about 4 hours (i.e., 30 µg/kg/day in rats, equivalent to 4.9 µg/kg/day in humans by allometry, but delivered over 4 hours, see Example 8). In some embodiments, 0.3 µg/kg/hour of CT38s (or similarly potent CRFR2 agonists) is delivered to the subject by subcutaneous infusion over about 3 hours (total dose=0.9 µg/kg). In other embodiments, the drug delivery rate is about 1 µg/kg/hour. In other embodiments, the delivery rate is not greater than about 2-3 µg/kg/hour. In some embodiments, the CRFR2 agonist is infused over a period not more than about 3 hours. In yet another embodiment, the CRFR2 agonist is infused over a period not more than about 2 hours. In another embodiment, the concentration is increased and the duration of dosing decreased (e.g., 1.7 µg/kg over 3 hours, and possibly less, by subcutaneous infusion).

Persons skilled in the art will understand that agonist concentrations, durations of dosing, and intervals of dosing specified in the present disclosure are patient-specific and are also affected by the route of administration and the potency of the specific CRFR2 agonist utilized. For example, subcutaneous infusion will take relatively more time to provide an intended concentration of a CRFR2 agonist to the brain as compared to intravenous infusion. Therefore, routes of administration associated with relatively slower drug delivery (and/or relatively faster drug clearance from the system) can require longer treatment periods (i.e., longer periods of drug infusion and/or more repetitions) as compared to routes of administration associated with relatively faster drug delivery (and/or relatively slower drug clearance from the system). Routine experiments may be employed to characterize the pharmacokinetics and pharmacodynamics of a CRFR2 agonist dosed via a certain route of administration, and such data would permit conversion of dosing parameters (e.g., dose concentration, treatment length, interval) between different routes of administration.

In other embodiments, the dosing paradigm utilizes a relatively low level priming bolus dose of ~0.05-0.1 µg/kg of body weight of the CRFR2 agonist, to achieve the desired minimum plasma concentration of the CRFR2 agonist rapidly. In such embodiments, the priming dose is administered before the controlled release of the CRFR2 agonist. In other embodiments, the priming dose is delivered in an escalating fashion, where following some level of initial dosing (and CRFR2 endocytosis), the dose level is increased to a level that might have been considered unsafe, (e.g., in terms of changes in heart rate, blood pressure or body temperature) before achieving some level of endocytosis, but would not be unsafe due to such CRFR2 endocytosis (see Example 8). In other embodiments, the total dose can be spread over several sessions, or utilizes a sustained delivery methodology (such as a subcutaneous depot, transdermal patch or other drug delivery technology) to deliver the total dose in one (or a few) administrations. In all of these embodiments, the sufficiency of achieved receptor endocytosis would have to be tested via symptom reduction.

According to the present disclosure, a patient suffering from a FSS, such as SEID, with a high degree of symptom severity (e.g., as indicated by relatively greater degree of CRFR2 up-regulation), would receive a relatively lower CRFR2 agonist starting dose, which would be administered over relatively longer and/or more treatment periods. Conversely, a patient suffering from a FSS, such as SEID, with a mild degree of symptom severity (e.g., as indicated by relatively lower degree of CRFR2 up-regulation), would receive a relatively higher CRFR2 agonist starting dose, which would be administered over relatively shorter and/or fewer treatment periods.

In another aspect of this disclosure, CRFR2 endocytosis can occur to the extent that the receptor is present, i.e., unless the receptor is up-regulated/relocated to the neuronal membrane, it will be unaffected by sustained stimulation.

In another aspect, although a specific CRFR2 agonist (CT38 or CT38s) was used in Examples 1-9, Example 10 draws similar conclusions on the effects of sustained stimulation, but with other CRFR2-selective agonists such as Ucn2 and stresscopin (a putative precursor peptide of Ucn3), delivered by the intravenous route of administration in both healthy human subjects and stable congestive heart failure patients. Moreover, the notions set forth here relate to the natural process of endocytosis and are therefore relevant to all CRFR2 agonists that are at least more potent than CRF (and a body of published work shows the equivalence of CT38, and its close analogs, with the endogenous CRFR2 agonists, Ucn1, Ucn2 and Ucn3), and where the use of endocytosis is confined to situations involving a maladaptation (i.e., previously normal becoming dysfunctional), in which there is no innate driver to cause the maladaptation to reoccur immediately following treatment. The doses, concentrations and ranges here relate to CT38, delivered by the subcutaneous route of administration, but human equivalents for alternative CRFR2 agonists, routes of administration, etc., can be easily determined. Accordingly, in one embodiment, the CRFR2 agonist used can be selected from FIG. 11. In some embodiments, the CRFR2 agonist comprises the amino acid sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or combinations thereof. In some embodiments, the CRFR2 agonist comprises an amino acid sequence having 90%, 91%, 92%, 93% 94%, 95%, 96%, 97%, 98%, 99%, or 100% sequence identity to sequences of SEQ ID NOs. 1-8. In some embodiments, the CRFR2 agonist comprises an amino acid sequence according to the formula:

(SEQ ID NO: 8)
ZGPPISIDLPX$_{11}$X$_{12}$LLRKX$_{17}$IEIEKQEKEKQQAX$_{31}$X$_{32}$NAX$_{35}$X$_{36}$X$_{38}$X$_{39}$X$_{40}$ wherein: $X_{11}$ is selected from F, Y, L, I, and T; $X_{12}$ is selected from Q, W, and Y; $X_{17}$ is selected from V and M; $X_{31}$ is selected from T and A; $X_{32}$ is selected from N and T; $X_{35}$ is selected from R and L; $X_{36}$ is selected from L and I; $X_{38}$ is selected from D and A; $X_{39}$ is selected from T and R; $X_{40}$ is selected from I and V, and wherein Z (i.e., Glx or Pyrrolidone carboxylic acid) is used to indicate N-terminal glutamic acid or glutamine that optionally has formed an internal cyclic lactam. In other embodiments, an acetate salt of the CRFR2 agonist is used.

Since antagonist binding promotes endocytosis of some GPCRs, it is hypothesized that CRFR2 endocytosis may also be induced by treatment with a potent CRFR2-selective antagonist along the lines of the present disclosure. In some cases, CRFR2 endocytosis may also be induced by treatment with a potent CRFR2-selective antagonist different than SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or combinations thereof. In some cases, CRFR2 endocytosis may also be induced by treatment with a potent CRFR2-selective antagonist different to CT38s.

In certain aspects, the FSS, also termed bodily distress syndrome, is one of a group of etiologically-unexplained diseases, including SEID, fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), Gulf War Illness (GWI, sometimes Gulf War Syndrome) and others (e.g., non-ulcer dyspepsia, premenstrual syndrome, chronic pelvic pain, interstitial cystitis, low back pain, repetitive strain injury, atypical or non-cardiac chest pain, hyperventilation syndrome, tension headache, temporomandibular joint disorder, atypical facial pain, Globus syndrome, food hypersensitivity, sick building syndrome, etc.), which have been argued to represent a single underlying common basic syndrome. Such arguments note: (i) the extensive overlap of the core symptoms, e.g., fatigue, diffuse pain, general malaise and evidence of dysautonomia; (ii) that patients meeting criteria for one syndrome often meet criteria for other syndromes as well; (iii) that patients with different syndromes share non-symptom characteristics, e.g., a history of prior stressful life events, particularly at a young age; (iv) that all syndromes share common psychiatric comorbidities, mainly anxiety and depression disorders; (v) the evidence of gender bias wherein females are more at risk than males; (vi) the similar disease onset with patients being apparently normal until a known trigger, possibly cumulative, precipitates the symptom cascade; (vii) the common involvement of the stress response and the HPA axis; (viii) that putative mechanisms overlap, e.g., 5HT abnormalities are found in many of these syndromes; and (ix) the considerable overlap in modestly successful treatment strategies, especially those involving some form of active rehabilitation, such as cognitive behavioral therapy. Detractors of the concept of a single underlying disorder have argued that despite symptom similarities across these diseases, there are important differences, for which no plausible explanation exists. However, the topographical organization of the raphe nuclei (and their target regions), with subregion-specificity of both receptor expression (including CRFR1 and CRFR2) and co-localization with neurons expressing 5HT and other neurotransmitters and neuropeptides, is consistent with stress effects (via CRF) upon prior adaptations of CRFR2/CRFR1 expression giving rise to markedly varied release of 5HT and other neurotransmitters depending upon the precise location of the maladaptation(s). This is seen in animal models, where different types of stress can result in different stress-induced adaptations in receptor configurations and behavior. In humans, these systems are at the very core of emotion, personality and individuality, and the individual components of these systems are known to be associated with completely different functions (e.g., the periaqueductal gray is involved in pain modulation, the lateral septum is involved in the inhibition of anxiety). Given the biochemical complexity of these systems, and the rich spectrum of human emotional and behavioral response they enable, the present disclosure postulates that all these diseases arise from CRFR2/CRFR1-5HT maladaptations, with differences in both the level and precise location of such CRFR2/CRFR1-5HT maladaptations within the raphe nuclei and their targets accounting for the symptom differences seen within and across these diseases.

There is evidence of CRFR2/CRFR1-5HT maladaptations in FMS, PTSD, IBS, atypical depression and MCS. In FMS for instance, the defining characteristic of pain is explained by 5HT in the spinal cord and amygdala respectively contributing to sensitization of dorsal horn neurons and pain perception, and while FMS has been associated with low serum 5HT, increasing brain 5HT (via selective serotonin reuptake inhibitors) is ineffective. In animals, PTSD-like behavior has been linked to CRFR2 up-regulation in the BNST. In IBS, 5HT modulates peristalsis and intestinal motility and secretion, and stress can affect visceral sensitivity, permeability, intestinal microbiota and immunity of the gastrointestinal tract (partially demonstrated in Example 3). In atypical depression, an excess of brain 5HT is suggested by the fact that patients respond to monoamine oxidase inhibitors, and in particular the type A isoform, which preferentially deaminates 5HT (and also melatonin, epinephrine and norepinephrine). In MCS, there is evidence of reduced $5HT_{1A}$ binding potential in the amygdala and anterior cingulate.

Certain other diseases can be seen as special cases of the foregoing diseases. For instance, CLD shares virtually all of the clinical symptoms of SEID, except that the trigger is bacterial (via tick bite), but the bacterial infection can be seen as leading to CRFR2/CRFR1-5HT maladaptations in exactly the same way as a viral trigger would lead to CRFR2/CRFR1-5HT maladaptations in SEID. PANS and PANDAS can also be seen as special cases of SEID, since the trigger is streptococcal infection, and 5HT has been implicated in obsessive compulsive behavior characteristic of these diseases. Similarly, GWI, or even food hypersensitivity and sick building syndrome, can be seen as special cases of MCS.

In other aspects, the proposed treatment paradigms are used to treat conditions such as chronic pain, anxiety and addiction, which also arise at least in part from adaptations in the limbic system.

In other aspects, the proposed treatment paradigms are used to treat primary dysautonomia, including postural orthostatic tachycardia syndrome, neurocardiogenic syncope, multiple system atrophy, hereditary sensory and autonomic neuropathies, Holmes-Adie syndrome, and/or secondary dysautonomia, including autoimmune diseases such as lupus, multiple sclerosis, inflammatory bowel disease, rheumatoid arthritis, diabetes (type 1), celiac disease, Sjogren's syndrome, Parkinson's disease. Therefore, in certain other embodiments, a human patient having primary or secondary dysautonomia is treated by administering via a controlled release of a CRFR2 agonist according to the presently described dosing regimen directed to treat a FSS.

Dosage Forms and Pharmaceutics Compositions

In another aspect, the present disclosure provides a pharmaceutical composition comprising a bolus dose or a dosage form comprising a CRFR2 agonist described herein. The pharmaceutical composition can further comprise a pharmaceutical carrier or excipient.

The compositions can be formulated as pharmaceutical compositions to provide an effective amount of a composition comprising a CRFR2 agonist. The CRFR2 agonist can be the active ingredient in the formulated pharmaceutical composition.

The disclosure provides pharmaceutical compositions comprising (a) an amount of a CRFR2 agonist present in an amount that is a safe and effective in treating, reducing and/or alleviating a FSS, and (b) a pharmaceutically acceptable carrier.

The unit dosage form of the present compositions can be formulated in a variety of different forms. The unit dosage form can be formulated to accommodate various routes of administration. The unit dosage form can be formulated in liquid, gel, semi-liquid, semi-solid, cream, ornament, syrup, tonic, or solid form. The unit dosage form can be formulated as a tablet, a capsule, a mucoadhesive capsule, or a pill. The unit dosage form can be formulated as a food, a beverage, a semi-solid food, a dietary supplement, a drink, or an elixir. The unit dosage form can be formulated for intravenous or subcutaneous infusion.

In one embodiment, a controlled release or bolus dose or dosage form comprises a therapeutically effective body-weight adjusted CRFR2 agonist, or a derivative thereof, for administration to a subject. The controlled release or bolus dose or dosage form can comprise about 0.01 µg/kg, about 0.02 µg/kg, about 0.03 µg/kg, about 0.04 µg/kg, about 0.05 µg/kg, about 0.06 µg/kg, about 0.07 µg/kg, about 0.08 µg/kg, about 0.09 µg/kg, about 0.10 µg/kg, about 0.2 µg/kg, about 0.3 µg/kg, about 0.4 µg/kg, about 0.5 µg/kg, about 0.6 µg/kg, about 0.7 µg/kg, about 0.8 µg/kg, about 0.9 µg/kg, about 1.0 µg/kg, about 1.1 µg/kg, about 1.2 µg/kg, about 1.3 µg/kg, about 1.4 µg/kg, about 1.5 µg/kg, about 1.6 µg/kg, about 1.7 µg/kg, about 1.8 µg/kg, about 1.9 µg/kg, about 2.0 µg/kg, about 4.0 µg/kg, about 6.0 µg/kg, about 8.0 µg/kg, about 10.0 µg/kg, about 12.0 µg/kg, about 14.0 µg/kg, about 16.0 µg/kg, about 18.0 µg/kg, about 20.0 µg/kg, about 22.0 µg/kg, or about 24.0 µg/kg of CRFR2 agonist (CT38s or similarly potent CRFR2 agonists). In some embodiments, the controlled release or bolus dose or dosage form comprises between about 0.01 µg/kg to about 0.05 µg/kg of CRFR2 agonist (such as CT38s or similarly potent CRFR2 agonists). In some embodiments, the controlled release or bolus dose or dosage form comprises between about 0.05 µg/kg to about 0.50 µg/kg of CRFR2 agonist (CT38s or similarly potent CRFR2 agonists). In some embodiments, the controlled release or bolus dose or dosage form comprises between about 0.50 µg/kg to about 1.0 µg/kg of CRFR2 agonist (CT38s or similarly potent CRFR2 agonists). In some embodiments, the controlled release or bolus dose or dosage form comprises between about 1.0 µg/kg to about 1.2 µg/kg of CRFR2 agonist (CT38s or similarly potent CRFR2 agonists). In some embodiments, the controlled release or bolus dose or dosage form comprises between about 1.2 µg/kg to about 1.3 µg/kg of CRFR2 agonist (CT38s or similarly potent CRFR2 agonists). In some embodiments, the controlled release or bolus dose or dosage form comprises between about 1.3 µg/kg to about 1.5 µg/kg of CRFR2 agonist (CT38s or similarly potent CRFR2 agonists). In some embodiments, the controlled release or bolus dose or dosage form comprises between about 1.5 µg/kg to about 1.7 µg/kg of CRFR2 agonist (CT38s or similarly potent CRFR2 agonists). In some embodiments, the controlled release or bolus dose or dosage form comprises between about 1.7 µg/kg to about 2.0 µg/kg of CRFR2 agonist (CT38s or similarly potent CRFR2 agonists). In some embodiments, the controlled release or bolus dose or dosage form comprises between about 2.0 µg/kg to about 4.0 µg/kg of CRFR2 agonist (CT38s or similarly potent CRFR2 agonists). In some embodiments, the controlled release or bolus dose or dosage form comprises between about 4.0 µg/kg to about 6.0 µg/kg of CRFR2 agonist (CT38s or similarly potent CRFR2 agonists). In some embodiments, the controlled release or bolus dose or dosage form comprises between about 6.0 µg/kg to about 8.0 µg/kg of CRFR2 agonist (CT38s or similarly potent CRFR2 agonists). In some embodiments, the controlled release or bolus dose or dosage form comprises between about 8.0 µg/kg to about 10.0 µg/kg of CRFR2 agonist (CT38s or similarly potent CRFR2 agonists). In some embodiments, the controlled release or bolus dose or dosage form comprises between about 10.0 µg/kg to about 12.0 µg/kg of CRFR2 agonist (CT38s or similarly potent CRFR2 agonists). In some embodiments, the controlled release or bolus dose or dosage form comprises between about 12.0 µg/kg to about 14.0 µg/kg of CRFR2 agonist (CT38s or similarly potent CRFR2 agonists). In some embodiments, the controlled release or bolus dose or dosage form comprises between about 14.0 µg/kg to about 16.0 µg/kg of CRFR2 agonist (CT38s or similarly potent CRFR2 agonists). In some embodiments, the controlled release or bolus dose or dosage form comprises between about 16.0 µg/kg to about 18.0 µg/kg of CRFR2 agonist (CT38s or similarly potent CRFR2 agonists). In some embodiments, the controlled release or bolus dose or dosage form comprises between about 18.0 µg/kg to about 20.0 µg/kg of CRFR2 agonist (CT38s or similarly potent CRFR2 agonists). In some embodiments, the controlled release or bolus dose or dosage form comprises between about 20.0 µg/kg to about 22.0 µg/kg of CRFR2 agonist (CT38s or similarly potent CRFR2 agonists). In some embodiments, the controlled release or bolus dose or dosage form comprises between about 22.0 µg/kg to about 24.0 µg/kg of CRFR2 agonist (CT38s or similarly potent CRFR2 agonists).

In other embodiments, the controlled release or bolus dose or dosage form is formulated for use in treating and/or assessing the severity of a FSS in a subject in need thereof. In some embodiments, the bolus dose or dosage is formulated for subcutaneous administration. In other embodiments, the CRFR2 agonist comprises the amino acid sequence shown as set forth in FIG. 11. In some embodiments, the CRFR2 agonist comprises the amino acid sequence of SEQ ID NO:1, SEQ ID NO:2, SEQ ID NO:3, SEQ ID NO:4, SEQ ID NO:5, SEQ ID NO:6, or SEQ ID NO:7, or SEQ ID NO:8, or combinations thereof. In some cases, the polypeptide has a sequence having at least 90%, 91%, 92%, 93% 94%, 95%, 96%, 97%, 98%, 99%, or 100% sequence identity to sequences of SEQ ID NOs. 1-8 as shown in FIG. 11. In one embodiment, the controlled release or bolus dose or dosage form is a pharmaceutical composition comprising the protein having the sequence as set forth in FIG. 11 (e.g., SEQ ID NO: 1) and a pharmaceutically acceptable carrier.

In another aspect, the present disclosure provides compositions, pharmaceutical compositions, and dose amounts of a CRFR2 agonist. In one other embodiment, the pharmaceutical composition or dose amount comprises a polypeptide having the sequence as set forth in FIG. 11, or a sequence having at least about 90% sequence identity to the sequence of SEQ ID NO. 1. In some cases, the polypeptide has a sequence having at least 90%, 91%, 92%, 93% 94%, 95%, 96%, 97%, 98%, 99%, or 100% sequence identity to sequences of SEQ ID NOs. 1-8. In another embodiment, the dose amount is for a human patient based upon the weight of the patient. A therapeutically effective amount of an active agent required for use in therapy varies with the length of time that activity is desired, and the age and the condition of the patient to be treated, among other factors, and is ultimately determined by the attendant physician. In general, however, doses employed for human treatment typically are in the range of about 3 µg/kg to about 24 µg/kg per day, for example about 1 µg/kg to about 2.5 µg/kg per day or about 2.5 µg/kg to about 5 µg/kg per day. The dosage regimen may be adjusted to provide the optimal therapeutic response. The desired dose may be conveniently administered in a single controlled release, or as multiple controlled release doses administered at appropriate intervals, for example over two, three, four or more days. In some instances, dosage levels below the lower limit of the aforesaid range may be more than adequate, while in other cases still larger doses may be employed without causing any harmful side effect, e.g. by escalating as endocytosis is achieved.

A composition of the disclosure can be administered in a single controlled release dose, with the total duration of dosing governed by the level of patient dysfunction at the onset.

A composition of the disclosure can be administered in multiple controlled release doses. In such cases, the total duration of dosing is still governed by the level of patient dysfunction at the onset, and the number of doses and the dosing interval are set by convenience and/or a desire to reassess the level of patient dysfunction before commencing the next dose.

Due to inter-subject variability in both symptom severity and compound pharmacokinetics, individualization of dosing regimen is necessary for optimal therapy. Dosing for a compound of the disclosure can be found by routine experimentation in light of the instant disclosure.

In one other embodiment, the pharmaceutical composition or dose amount further comprises a pharmaceutically acceptable carrier.

In one other embodiment, the human patient is an adult. In one other embodiment, the human patient is a child. In one additional embodiment, the CRFR2 agonist is provided in the pharmaceutical composition, composition, or dose amount as a certain quantity. In another embodiment, the pharmaceutical composition comprising a CRFR2 agonist, or a derivative thereof, is provided in an amount between about 1 µg, about, 2 µg, about 3 µg, about 4 µg, about 5 µg, about 6 µg, about 7 µg, about 8 µg, about 9 µg, about 10 µg, about 12 µg, about 18 µg, or about 24 µg. In one other embodiment, the pharmaceutical composition or dose amount further comprises a pharmaceutically acceptable carrier.

It should be noted that reference is made to a composition, pharmaceutical composition or dose amount comprising an amount of $CRFR_2$ agonist between about a first µg and about a second µg, the "first µg" term may include the first µg value and the "second µg" term may include the second µg value.

Routes of Administration

An effective amount of a composition comprising a CRFR2 agonist, or derivatives thereof can be administered by various routes to modulate or reduce a FSS. An affective amount of the composition can be administered to a subject through a variety of different routes. Further examples of the accepted modes of administration of compositions having similar utilities can include: rectal, buccal, intranasal and transdermal routes, by intra-arterial injection, intravenously, intraperitoneally, parenterally, intramuscularly, subcutaneously, orally, topically, or as an inhalant. In some embodiments, the composition comprising a CRFR2 agonist or derivatives thereof is administered via controlled release selected from subcutaneous infusion, intravenous infusion, gastrointestinal delivery, transmucosal and transdermal patch delivery. The controlled release can comprise a continuous delivery methodology.

The compositions comprising a CRFR2 agonist herein are formulated for administration to a subject. The composition formulation can depend in part on the route of administration.

Combination

The agonists or compositions described herein can be formulated or co-administered in conjunction with other therapeutic agents. Exemplary additional therapeutic agents useful for combination therapy include, but are not limited to, a CRFR1 agonist and a corticosteroid. In some embodiments, a CRFR2 agonist is administered according to the methods described herein in combination with a CRFR1 agonist, and/or a corticosteroid (or cortisol). In other embodiments instead of a combination consisting of a CRFR2 agonist and a CRFR1 agonist, a single agonist that is selective for both CRFR1 and CRFR2 can be utilized.

Pharmaceutical Composition for Injection

The disclosure further provides a composition for injection containing a CRFR2 agonist or any analogs or derivatives thereof. The composition can be a pharmaceutical composition suitable for injection. The composition can further comprise a pharmaceutical excipient suitable for injection.

The forms in which the composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

The composition formulated for injection can include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate.

Aqueous solutions in saline are also conventionally used for injection. Aqueous carriers include water, alcoholic/aqueous solutions, emulsions or suspensions, including saline and buffered media. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

A composition formulated for injection can comprise parenteral vehicles, preservatives and other additives. Parenteral vehicles include sodium chloride solution, Ringer's dextrose, dextrose and sodium chloride, lactated Ringer's, or fixed oils. Preservatives and other additives may also be present such as, for example, antimicrobials, anti-oxidants, chelating agents, and inert gases and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional ingredient from a previously sterile-filtered solution thereof.

Pharmaceutical Composition for Topical (e.g., Transdermal) Delivery

The disclosure further provides a composition for transdermal delivery containing a CRFR2 agonist, or any analog or derivatives thereof suitable for transdermal delivery. The composition may be a pharmaceutical composition for transdermal delivery. The composition may further comprise a pharmaceutical excipient suitable for transdermal delivery.

Composition of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions, and powders. In general, carriers with higher densities are capable of providing an area with a prolonged exposure to the active ingredients. Conventional pharmaceutical carriers, aqueous, powder or oily bases, thickeners and the like may be useful or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, mucoadhesive capsule, intravenous drips, pump device, or any bio-engineered materials. A solution formulation may provide more immediate exposure of the active ingredient to the chosen area.

The pharmaceutical composition also may comprise suitable solid or gel phase carriers or excipients, which are compounds that allow increased penetration of, or assist in the delivery of, therapeutic molecules across the stratum corneum permeability barrier of the skin. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for administering the composition can employ transdermal delivery devices ("patches"). Such transdermal patches may be used to provide continuous or discontinuous infusion of a compound of the present disclosure in controlled amounts, either with or without another agent.

The construction and use of transdermal patches for the delivery of pharmaceutical agents have been established. See, e.g., U.S. Pat. Nos. 5,023,252, 4,992,445 and 5,001,139. Such patches may be constructed for continuous, pulsatile, or on demand delivery of pharmaceutical agents.

Other Pharmaceutical Compositions

A pharmaceutical composition may also be prepared from compositions described herein and one or more pharmaceutically acceptable excipients suitable for sublingual, intravaginal, buccal, rectal, intraocular, intranasal, epidural, or intraspinal administration. Preparations for such pharmaceutical composition have been reported elsewhere.

Dosages and Administration Regimens

An effective amount of a CRFR2 agonist, or any analog or derivatives thereof may be administered to a subject in need thereof according to various dosing regimens. A composition comprising the effective amount of a CRFR2 agonist, or any analog or derivatives thereof may be administered in single dose or in more than one dose. The effective amount of a CRFR2 agonist, or any analog or derivatives thereof may be administered in about one dose to about 28 doses. The composition can be administered in more than one dose. In some embodiments the composition can be administered in more than one dose with an increase of dose unit sequentially.

Administration can be initiated at the onset of a FSS or at a time after disease onset. The compositions comprising a CRFR2 agonist, or any analog or derivatives thereof can be administered to a subject who is diagnosed with a FSS. In some embodiments, the FSS is systemic exertion intolerance disease (SEID). In other embodiments, the FSS is fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), Gulf War Illness (GWI, sometimes Gulf War Syndrome). The composition can be administered to the subject over a period of time. As one example, the composition can be administered to the subject for a period of time from between about 1.0 hour to about 8.0 hours, between about 1.5 hours to about 6.5 hours, between about 2.0 hours to about 4 hours, between about 3.0 hours to about 4.0 hours, between about 3.5 hours to about 5.0 hours, or between about 2.5 hours to about 7.5 hours. The composition can be administered to the subject over a period of time of no more than 1 hour, 1.2 hours, 1.4 hours, 1.6 hours, 1.8 hours, 2.0 hours, 2.2 hours, 2.4 hours, 2.6 hours, 2.8 hours, 3.0 hours, 3.2 hours, 3.4 hours, 3.6 hours, 3.8 hours, 4.0 hours, 4.2 hours, 4.4 hours, 4.6 hours, 4.8 hours, 5.0 hours, 6 hours, 7 hours, 8 hours, 9 hours, 10 hours, 12 hours, 24 hours, or 48 hours.

As another example, the composition can be administered to the subject from between about 1 minute to about 60 minutes, between about 5 minutes to about 50 minutes, between about 20 minutes to about 40 minutes, between about 30 minutes to about 45 minutes, between about 35 minutes to about 55 minutes, or between about 2 minutes to about 20 minutes. The composition can be administered to the subject over a period of time of no more than 1 minute, 2 minutes, 4 minutes, 6 minutes, 8 minutes, 10 minutes, 20 minutes, 30 minutes, 40 minutes, 50 minutes, or 60 minutes.

The composition can be administered to the patient by controlled release over at least one treatment period. For example, the composition can be administered to the patient by controlled release over a period from between about 1 hour to about 48 hours, between about 3 hours to about 4 hours, between about 8 hours to about 12 hours, between about 24 hours to about 48 hours, between about 2 hours to 5 hours, between about 6 hours to about 8 hours. In some embodiments, the composition is administered to the patient by controlled release over a period from between about 3 hours to about 4 hours. In some embodiments, the composition is administered to the patient by controlled release over a period from between about 8 hours to about 12 hours. In some embodiments, the composition is administered to the patient by controlled release over a period from between about 24 hours to about 48 hours.

The composition can be administered to the patient by controlled release over separate treatment periods. For example, the composition can be administered to the patient by controlled release over 1 to 28, 2 to 25, 4 to 20, 5 to 15, or 2 to 12, separate treatment periods. The composition can be administered to the patient by controlled release over 2 to 6 separate treatment periods, wherein each period lasts from between about 1 hour to about 48 hours, between about 3 hours to about 4 hours, between about 8 hours to about 12 hours, between about 24 hours to about 48 hours, between about 2 hours to 5 hours, between about 6 hours to about 8 hours. In some embodiments, the composition is administered to the patient by controlled release over a period from between about 3 hours to about 4 hours. In some embodiments, the composition is administered to the patient by controlled release over a period from between about 8 hours to about 12 hours. In some embodiments, the composition is administered to the patient by controlled release over a period from between about 24 hours to about 48 hours.

Articles of Manufacture

The disclosure also provides kits. The kits include a compound or composition of the present disclosure as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials.

Another aspect of this invention, contemplates a kit comprising a supply of the CRFR2 agonist, together with an apparatus for delivering both a bolus (to facilitate the determination of minimum stimulating bolus dose), as well as an infusion (to bring about receptor endocytosis).

In another aspect, the present invention also provides kits and articles of manufacture containing materials useful for the treatment and/or diagnosis of disease (e.g., FSS). In another embodiment, the invention provides kits, comprising packaging material and at least a first container comprising a dosage form or pharmaceutical composition of the foregoing embodiments and a label identifying the dosage form or pharmaceutical composition and storage and handling conditions, and a sheet of instructions for the reconstitution and/or administration of the dosage form or pharmaceutical compositions to a subject. In one other embodiment, the kit includes a container and a label, which can be located on the container or associated with the container. The container may be a bottle, vial, syringe, cartridge (including autoinjector cartridges), or any other suitable container, and may be formed from various materials, such as glass or plastic. The container holds a composition having a CRFR2 agonist, an analog or derivative thereof, and can have a sterile access port. Examples of containers include a vial with a stopper that can be pierced by a hypodermic injection needle. The kits may have additional containers that hold various reagents, e.g., diluents, preservatives, and buffers. The label may provide a description of the composition as well as instructions for the intended use.

In one other aspect, the container is a pre-filled syringe. In one embodiment, the syringe is pre-filled with a composition having a CRFR2 agonist as described herein. In one additional aspect, the present invention provides containers of the composition having a CRFR2 agonist as described herein, wherein the container is suitable for autoinjection of the composition. In one embodiment, the container is a cartridge. In another embodiment, the container is a cartridge in an autoinjection pen. Other suitable autoinjection devices may be used for the present invention. In some embodiments, the autoinjection device comprises a spring-loaded syringe within a cylindrical housing that shields the needle tip prior to injection. In one embodiment, the patient depresses a button on the device and the syringe needle is automatically inserted to deliver the contents.

In another embodiment, the device is a gas jet autoinjection device. In other embodiments, the gas jet device comprises a cylinder of pressurized gas but the needle is absent. Upon activation, the device propels a fine jet of liquid through the skin without the use of a needle. In one other embodiment, the device is an iontophoresis device or electromotive drug administration (EMDA) device (e.g., use of a small electric charge to deliver an agent through the skin without the use of a needle).

The kit has at least one container that includes a molecule comprising CRFR2 agonist described herein as the active agent. The container may comprise CRFR2 agonist dosage form or pharmaceutical composition. A label may be provided indicating that the dosage form or composition may be used to treat a disease. The label may also provide instructions for administration to a subject in need of treatment. The kit may further contain an additional container having a pharmaceutically-acceptable buffer, such as bacteriostatic water for injection (BWFI), phosphate-buffered saline, Ringer's solution and dextrose solution. Finally, the kit may also contain any other suitable materials, including other buffers, diluents, filters, needles, and syringes.

In one aspect, the present invention provides a kit comprising a container which holds a pharmaceutical composition for administration to a human patient comprising a CRFR2 agonist. In one embodiment, the CRFR2 agonist comprises an amino acid sequence having at least about 90% sequence identity to one of the sequences set forth in FIG. 11. In another embodiment, the kit further comprises a package insert associated with said container. In one other embodiment, the package insert indicates that said composition is for the treatment of SEID or a FSS, by administration of more than one dose of the composition.

The kit may comprise an effective amount of a composition comprising a CRFR2 agonist. The kit may further comprise instructions for intravenously administering an effective amount of the composition to treat or alleviate a FSS.

Suitable packaging and additional articles for use (e.g., measuring cup for liquid preparations, foil wrapping to minimize exposure to air, and the like) may be included in the kit. Kits described herein can be provided, marketed and/or promoted to health providers, including physicians, nurses, pharmacists, formulary officials, and the like. Kits may also be marketed directly to the consumer.

While preferred embodiments of the present invention are shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Examples included below demonstrate the therapeutic potential of delivering a CRFR2 agonist.

EXAMPLES

Experimental work with proprietary CRFR2 agonists, including CT38 (originally "PG-873638"), CT38s (acetate salt of CT38, originally "PG-968041"), CT37 (originally "PG-873637"), among others—each approximately equivalent in potency and pharmacokinetic parameters to endogenous Ucn2—have shown that certain properties, such as the effects on heart rate and blood pressure, which are similar to those induced by Ucn2, can be attenuated via sustained stimulation of the receptor, which presumably leads to persistent receptor desensitization or endocytosis (internalization). In general, the following experiments dosed either CT38 or CT38s, but plasma concentrations were measured in terms of CT38 (free base).

Example 1-Effects on Maximum Heart Rate, Minimum Mean Arterial Blood Pressure, and Minimum Body Temperature Induced by Subcutaneously-Administered Bolus Doses of a Proprietary CRFR2 Agonist (CT38s) in Normal Rats In an experiment (645.80-54795), male Sprague Dawley rats were dosed by the subcutaneous route of administration, with a single daily bolus of either vehicle or CT38s at varying dose levels, with each animal receiving all doses (in a Latin square dosing pattern). The purpose of this experiment was to investigate the effects of CT38s on heart rate, blood pressure and temperature (monitored via implanted telemetry devices).

FIGS. 1A, 1B and 1C respectively show that bolus dosing of CT38s caused significant dose-responsive increases in heart rate (maximal relative to vehicle at 30 mins post-dose, returning to control values by 4 hours post-dose), decreases in blood pressure (minimal relative to vehicle at 30 mins post-dose, returning to control values by 4 hours post-dose) and decreases in body temperature (minimal relative to vehicle at 1 hour post-dose, returning to control values by 8 hours post-dose), in normal rats.

Example 2-Effect on Respiratory Rate Induced by Subcutaneously-Administered Bolus Doses of a Proprietary CRFR2 Agonist (CT38s) in Normal Rats In an experiment (645.80-54313), male Sprague Dawley rats were dosed by the subcutaneous route of administration, with a single bolus of either vehicle, CT38s at varying dose levels, or morphine (positive control). The purpose of this experiment was to investigate the effects of CT38s on respiratory rate and tidal volume (monitored in body enclosed plethysmography chambers designed to isolate the head from body respiratory movements via transducers).

FIG. 2 shows that bolus dosing of CT38s caused significant dose-responsive decreases in respiratory rate (at 1 hour post-dose, returning to control values by 2 hours post-dose, with smaller changes in tidal volume, not shown), in normal rats.

Example 3-Effect on Gastrointestinal Transit Induced by Subcutaneously-Administered Bolus Doses of a Proprietary CRFR2 Agonist (CT38s) in Normal Rats In an experiment (645.80-54473), male Sprague Dawley rats were dosed by the subcutaneous route of administration, with a single bolus of either vehicle or CT38s at varying dose levels. The purpose of this experiment was to investigate the effects of CT38s on gastrointestinal transit for a charcoal meal (measured as ratio of the distance traveled by the charcoal to the length of the intestine, following euthanasia).

FIG. 3 shows that bolus dosing of CT38s caused significant dose-responsive delays in gastrointestinal transit (at 30 mins post-dose), in normal rats.

Example 4-Effect on Urine Volume Induced by Subcutaneously-Administered Bolus Doses of a Proprietary CRFR2 Agonist (CT38s) in Normal Rats In an experiment (645.80-54315), male Sprague Dawley rats were dosed by the subcutaneous route of administration, with a single bolus of either vehicle or CT38s at varying dose levels. The purpose of this experiment was to investigate the effects of CT38s on renal function (measured by urine volume and chemistry via metabolic cages designed for the collection of urine).

FIG. 4 shows that bolus dosing of CT38s caused significant dose-responsive changes in renal function (decreased urinary volume and electrolyte excretion at 0-4 hours post-dose, and increased urinary volume and electrolyte excretion at 4-8 hours post-dose), in normal rats.

Example 5-Effect on Norepinephrine and Corticosterone Secretion Induced by Subcutaneously-Administered Bolus Doses of a Proprietary CRFR2 Agonist (CT38) in Normal Rats In an experiment (640.80-53879), male Sprague Dawley rats were dosed by the subcutaneous route of administration, with a single bolus of either vehicle or CT38. The purpose of this experiment was to investigate the effects of CT38 on stress hormones, epinephrine, norepinephrine, corticosterone and aldosterone (measured via venous blood samples, collected at different time points via an indwelling jugular catheter, intended to minimize stress and variability for the measurement of stress hormones).

FIG. 5 shows that bolus dosing of CT38 caused significant increases in norepinephrine and corticosterone (at 2 hours post-dose, returning to control values at 4 hours post-dose), in normal rats. Note that norepinephrine and corticosterone levels are measured in ng/ml and µg/ml, respectively. Changes in epinephrine and aldosterone were not significant.

Example 6-Effects on Total Distance Traveled and Number of Vertical Movements Induced by Subcutaneously-Administered Bolus Doses of a Proprietary CRFR2 Agonist (CT38s) in Normal Rats In an experiment (645.80-54311), male Sprague Dawley rats were dosed by the subcutaneous route of administration, with a single bolus of either vehicle or CT38s at varying dose levels. The purpose of this experiment was to investigate the effects of CT38s on spontaneous motor activity (measured as total distance traveled and number of vertical movements via activity monitoring system in light and dark cages).

FIGS. 6A and 6B show that bolus dosing of CT38s caused significant dose responsive decreases in total distance traveled and in the number of vertical movements, in normal rats.

Example 7-Effects on Maximum Heart Rate, Minimum Mean Arterial Blood Pressure and Minimum Body Temperature Induced by the Maximum or Steady State Plasma Concentrations (Cmax or Css) of a Single Dose of a Proprietary CRFR2 Agonist (CT38), Subcutaneously-Administered Either by Bolus (Triangles, Dashed Lines) or by Continuous Infusion (Circles, Solid Lines), in Normal Rats In 4 separate experiments (645.80-54795, 640.80-53144, 645.80-56569, 640.80-53180), male and female Sprague Dawley rats were dosed by the subcutaneous route of administration, with either a single daily bolus or a continuous infusion (via osmotic minipump over 24 or 72 hours), of either vehicle, CT38s or CT38 at varying dose levels. The purpose of these experiments was to compare the effects of plasma concentrations and exposure (measured in terms of CT38) on heart rate, blood pressure and temperature (monitored via implanted telemetry devices), when dosed either instantaneously (bolus) or continuously (infusion). The time(s) to reach maximum or steady state plasma concentrations, by instantaneous (bolus) and continuous (infusion) dosing, were ~0.6 and ~5.2 hours, respectively.

FIGS. 7A, 7B and 7C show that the duration of dosing affected the ability of CT38 to induce changes in heart rate, blood pressure and body temperature. At low plasma concentrations (~1 ng/ml and below), regardless of the duration of dosing, escalating CT38 plasma concentrations increased heart rate and decreased blood pressure and body temperature (very slightly). At high plasma levels (~11 ng/ml and above), regardless of the duration of dosing, escalating CT38 plasma concentrations reversed the effects seen at low levels, i.e., a loss of the ability to induce an increase in heart rate or a decrease in blood pressure and body temperature. At intermediate plasma levels (between ~1 and ~11 ng/ml), instantaneous dosing (bolus) caused an increase in heart rate and a decrease in blood pressure and body temperature, while continuous dosing (infusion) resulted in a loss of the ability to induce an increase in heart rate or a decrease in blood pressure or body temperature.

More specifically, for a given plasma concentration of CT38, in the range of ~0.3 to ~3.0 ng/ml in rats, sustained stimulation of CRFR2 (infused dosing) minimized the effects on heart rate, while transient stimulation (bolus dosing) did not—blood pressure and body temperature effects within this range were manageable.

The magnitude of the induced changes in heart rate, blood pressure and body temperature in FIGS. 7A, 7B and 7C, likely resulted from the balance between direct agonist effect (dependent upon the concentration of the CRFR2 agonist) and the loss of agonist effect, both via metabolism (reducing the concentration of the agonist) as well as CRFR2 endocytosis (reducing the availability of the receptor). Independent in vitro studies show that CRFR2 endocytosis occurs via agonist-specific mechanisms, at a rate governed by time, the agonist potency and agonist concentration at the receptor, itself dependent upon the agonist half-life (fixed for a given agonist), route of administration and whether or not the stimulation of the receptor is transient (such as via bolus dosing) or sustained (such as via infused dosing). Thus for the specific agonist (CT38) and route of administration (subcutaneous) in Example 7, for a given agonist concentration at the receptor, differences between bolus and infused dosing were attributable solely to the duration of CRFR2 stimulation.

The heart rate under stress (but not the tonic regulation) is modulated by CRFR2 in the BNST. Thus, FIG. 7A suggests that when administered by instantaneous (bolus) dosing, i.e., short duration of dosing, low to intermediate plasma concentrations of CT38 were sufficiently intense to stimulate CRFR2 and increase the heart rate in a dose-responsive manner, but were not sufficiently intense to induce CRFR2 endocytosis in the BNST; while high plasma concentrations of CT38 were sufficiently intense to induce CRFR2 endocytosis in the BNST, but only after initially causing large, unacceptable increases in the heart rate. In contrast, when administered by continuous (infusion) dosing, i.e., prolonged duration of dosing, low plasma concentrations of CT38 were sufficiently intense to stimulate CRFR2 and increase the heart rate in a dose-responsive manner, but were insufficiently intense to induce CRFR2 endocytosis in the BNST; intermediate plasma concentrations of CT38 were sufficiently intense and prolonged to induce CRFR2 endocytosis in the BNST without causing large increases in the heart rate; and high plasma concentrations of CT38 were sufficiently intense and/or sufficiently prolonged to induce CRFR2 endocytosis in the BNST without causing large increases in the heart rate. Thus, the lowest concentration of a 24-hour subcutaneous infusion of CT38 that caused CRFR2 endocytosis in the BNST of rats (i.e., where the curve for continuous dosing passes through the point of maximum heart rate decrease) was ~1.0-2.0 ng/ml of sustained stimulation in rats, or a human equivalent of 1.1-1.6 ng/ml (based on pharmacokinetic-pharmacodynamic modeling, using human data from Example 9). The lowest concentration of a subcutaneous bolus of CT38 to induce CRFR2 endocytosis in the BNST of rats (i.e., where the curve for instantaneous dosing passes through the point of maximum heart rate increase) was 20.0 ng/ml (or a human equivalent of ~3.2 ng/ml based on pharmacokinetic-pharmacodynamic modeling, using human data from Example 9), but only after inducing unacceptable changes in heart rate, blood pressure and body temperature.

Like other CRFR2 agonists, CT38 caused a decrease in blood pressure that has been shown to result from the combined effects of CRFR2-induced vasodilation in the cardiovascular system and reduced cardiac output in response to CRFR2-induced increases in the heart rate. FIG. 7B supports this notion. That is, when administered by instantaneous (bolus) dosing, low to intermediate plasma concentrations of CT38, which were insufficient to induce CRFR2 endocytosis in the BNST, resulted in dose-responsive decreases in blood pressure, representing the combined effects of vasodilation and reduced cardiac output. Similarly, when administered by continuous (infusion) dosing, low plasma concentrations of CT38, which were insufficient to induce CRFR2 endocytosis in the BNST, also resulted in dose-responsive decreases in blood pressure, representing the combined effects of vasodilation and reduced cardiac output. In contrast however, when administered by continuous (infusion) dosing, intermediate plasma concentrations of CT38, which were sufficient to induce CRFR2 endocytosis in the BNST and a loss of the heart rate effect, the blood pressure effect was only slightly diminished, probably reflecting vasodilation, but not reduced cardiac output. Thus, FIG. 7B suggests that CRFR2 endocytosis did not occur within the cardiovascular system.

Importantly, the fact that continuous (infusion) dosing likely induced endocytosis within the BNST, but not within the cardiovascular system, suggests that the BNST is prone to persistent adaptation, while the cardiovascular system is not.

Body temperature is controlled by the release of 5HT in the medial preoptic area of the hypothalamus, specifically involving post-synaptic $5HT_2$ receptors and presynaptic $5HT_{1A}$ receptors. FIG. 7C identifies the lowest concentration of a 24-hour subcutaneous infusion of CT38 that caused CRFR2 endocytosis in the medial preoptic area of the hypothalamus of rats (i.e., where the curves for instantaneous and continuous dosing separate) was ~1.0-3.0 ng/ml of sustained stimulation in rats, or a human equivalent of 1.1-1.9 ng/ml (based on pharmacokinetic-pharmacodynamic modeling, using human data from Example 9). The lowest concentration of a subcutaneous bolus of CT38 to induce CRFR2 endocytosis in the medial preoptic area of the hypothalamus of rats (i.e., where the curve for instantaneous dosing approaches the minimum temperature) was 20.0 ng/ml (or a human equivalent of ~3.2 ng/ml based on pharmacokinetic-pharmacodynamic modeling, using human data from Example 9), but only after inducing intolerable changes in heart rate, blood pressure and body temperature.

Example 8-Effects on Maximum Heart Rate and Minimum Mean Arterial Blood Pressure Induced by the Steady State Plasma Concentrations (Css) of an Escalating Dose of a Proprietary CRFR2 Agonist (CT38), Subcutaneously-Administered by Continuous Infusion (without Cessation of Dosing) in Normal Rats In an experiment (640.80-53180), female Sprague Dawley rats were dosed by the subcutaneous route of administration, continuously via catheter, commencing at a dose of 0 μg/kg/day (vehicle) and escalating consecutively through 30, 300, 1,000 and 10,000 μg/kg/day of CT38, with each dose being maintained for 72 hours without cessation of dosing. The purpose of this experiment was to understand the effects of CT38 on heart rate, blood pressure and temperature (monitored via implanted telemetry device), when dosed continuously (infusion) over prolonged periods.

FIG. 8 shows the average heart rate and average mean arterial blood pressure at steady state plasma concentrations (i.e., 5 hours after the onset of dosing when steady-state was achieved), for each dose level. The heart rate data of FIG. 8A further emphasized that sustained stimulation of CRFR2 (via continuous infusion) reduced the ability of a CRFR2 agonist to induce a heart rate increase, but in a progressive, time-dependent manner. That is, after 72 hours of sustained stimulation at a given dose-level, escalation to the next the dose level was unable to increase the heart rate to prior levels, despite rising plasma concentrations. Moreover, over a 15-day period of sustained stimulation, there was no evidence to suggest receptor resensitization. This diminishment of CRFR2-induced (or stress-induced) effect on the heart rate (FIG. 8A), was not accompanied by a corresponding diminishment of blood pressure or vasodilatory effect (FIG. 8B), further supporting the notion that CRFR2 endocytosis occurred in the BNST, but not in the cardiovascular system.

Also, though not shown in FIG. 8A, when dosed at 30 μg/kg/day (first dose of CT38), the plasma concentration would have reached 1.30 ng/ml within ~4 hours. This is the plasma concentration at which CT38 caused tachycardia when dosed by instantaneous (bolus) dosing, but the absence of any observed tachycardia suggested that some CRFR2 endocytosis had already occurred within 4 hours.

Example 9-Effects on the Maximum Heart Rate and Minimum Mean Arterial Blood Pressure Induced by the Maximum Plasma Concentration (Cmax), and on the Time-Specific Heart Rate Induced by the Plasma Concentration (C), of a Single Ascending Dose of a Proprietary CRFR2 Agonist (CT38), Subcutaneously-Administered by Bolus in Healthy Human Subjects In a Phase 1 human single ascending dose clinical trial (2005051), CT38s was dosed by subcutaneous injection (bolus) in cohorts of human subjects (each cohort receiving the same dose; rising dose across cohorts). The purpose of this trial was to determine the maximum tolerated bolus dose of CT38s in healthy human subjects.

FIG. 9 shows the maximum plasma concentration of CT38 resulting from a subcutaneous injection and its effects on the maximum heart rate (FIG. 9A) and minimum mean arterial blood pressure (FIG. 9B) of healthy male subjects. FIG. 9C shows the plasma concentration of CT38 (lines read on left axis) and the heart rate (bars read on right axis), at specific points in time (grey to black color representing increased CT38s dose level).

Given the single instantaneous (bolus) nature of administration, and the avoidance of high plasma concentrations, this trial did not, and was not expected to achieve any CRFR2 endocytosis. The trial did show that bolus-induced changes in the heart rate and blood pressure in humans closely mirror those observed in rats, suggesting that continuous (infusion) dosing in humans approximates that in rats. Example 9 established the plasma concentration profile of a subcutaneously-administered bolus of CT38s, in humans, enabling pharmacokinetic-pharmacodynamic predictions based on rat studies. The lowest maximum plasma concentrations (Cmax) of CT38 to cause statistically significant increases in the heart rate, tachycardia (defined as 100 beats/minute) and decreases in blood pressure were 0.32 ng/ml (at a dose of 0.200 µg/kg of body weight), 1.56 ng/ml (at a doses of 0.833 µg/kg of body weight) and 2.46 ng/ml (at a dose of 1.667 µg/kg of body weight), respectively. FIG. 9C established the concentration rate parameters that resulted in increased heart rate. Specifically, a rapid rate of introduction of CT38s, achieving plasma concentrations in excess of ~0.2 ng/ml in any 15-minute period, caused increased heart rate (likely because endocytosis did not occur).

Example 10-Effects on Maximum Heart Rate Induced by the Maximum or Steady State Plasma Concentrations of Various CRFR2 Agonists, Including a Proprietary CRFR2 Agonist (CT38s), Urocortin 2 and Stresscopin, in Either Healthy Human Subjects or Stable Congestive Heart Failure Patients In independent clinical trials Ucn2 was intravenously infused over 1 hour, in healthy human subjects and in stable congestive heart failure patients. In another independent clinical trial, stresscopin (a putative precursor peptide of Ucn3) was intravenously infused over 3 hours, escalating through 3 dose levels. The published data from these trials, together with the data from Example 9, are combined in FIG. 10, which shows the maximum heart rate resulting from the maximum or steady state plasma concentrations (Cmax or Css, respectively) of either: (i) CT38 administered by subcutaneous injection (bolus) in healthy male subjects (triangles, solid line); or (ii) Ucn2 administered by intravenous infusion over 1 hour in either healthy human subjects (circles, solid line) or stable congestive heart failure patients (circles, dashed line); or (iii) stresscopin (SCP) administered by escalating intravenous infusion (3 dose levels) over 3 hours in stable congestive heart failure patients (circles, dashed line). The table of FIG. 10 shows that Ucn2 and CT38 exhibit very similar in vitro binding potential for CRFR2 (maximal, at low concentrations) and CRFR1 (minimal, at high concentrations), and have similar half-lives in vivo (rats). Ucn3, a proxy for SCP, also exhibits strong binding potential for CRFR2 (maximal, at low concentrations), but weak binding potential for CRFR1 (minimal, at moderate concentrations).

FIG. 10 demonstrates that where an instantaneous (bolus) plasma concentration of a CRFR2 agonist (CT38) induced an increasing effect on the heart rate of healthy humans, this effect was much diminished under continuous (infusion) plasma concentrations of a CRFR2 agonist with similar pharmacokinetic and pharmacodynamic properties (Ucn2)—resembling the separation of the curves for bolus and infused dosing (at ~0.3 ng/ml) in FIG. 7A. Moreover, the pattern of Ucn2 effect on the heart rate of healthy subjects did not change in stable congestive heart failure patients, which itself was very similar to that observed with stresscopin (approximately equipotent with Ucn3). That is, for strongly potent CRFR2 agonists and relative intermediate plasma concentrations, the loss of the ability to induce a heart rate increase via continuous dosing, was driven by the duration of dosing, and appeared to occur with different selective CRFR2 agonists (e.g., Ucn2, stresscopin), irrespective of the condition of the human subject. The sequences of these CRFR2 agonists are shown in FIG. 11.

EMBODIMENTS

The following non-limiting embodiments provide illustrative examples of the invention, but do not limit the scope of the invention Embodiment 1

A method for treating a functional somatic syndrome (FSS) comprising administering to a human patient in need of such treatment a safe and effective amount of a corticotropin-releasing factor receptor subtype 2 (CRFR2) agonist Embodiment 2

The method of embodiment 1, wherein the administering is effective to achieve a minimum plasma concentration of the CRFR2 agonist greater than the minimum endocytotic concentration of the CRFR2 agonist in the human patient, and wherein the minimum plasma concentration is maintained over at least one treatment period.

Embodiment 3

The method of embodiment 2, wherein the minimum plasma concentration of the CRFR2 agonist is at least about 1.1-1.9 ng/ml.

Embodiment 4

The method of any one of embodiments 1-3, wherein the duration of the at least one treatment period is selected from the group consisting of about 0.5-2 hours, about 2-3 hours, about 3-4 hours, about 4-8 hours, about 8-12 hours, about 12-24 hours, and about 24-48 hours.

Embodiment 5

The method of any one of embodiments 1-4, wherein the minimum plasma concentration is maintained over two or more separate treatment periods.

Embodiment 6

The method of any one of embodiments 1-5, wherein the minimum plasma concentration is maintained over 2 to 28 separate treatment periods.

Embodiment 7

The method of embodiment 5 or embodiment 6, wherein the separate treatment periods are separated by a period of time sufficient to ensure that the plasma concentration of the CRFR2 agonist is no longer detectable in the human patient.

Embodiment 8

The method of any one of embodiments 5-7, wherein the duration of a treatment period is adjusted in a subsequent treatment in the same patient.

Embodiment 9

The method of any one of embodiments 1-8, wherein the CRFR2 agonist is administered at a rate that does not increase the plasma concentration of the agonist in the human patient by more than a maximum rate in any 15-minute time window within any treatment period.

Embodiment 10

The method of embodiment 9, wherein the maximum rate is no more than about 0.2 ng/ml in any 15-minute time window within any treatment period.

Embodiment 11

The method of any one of embodiments 1-10, wherein the administering is by controlled release.

Embodiment 12

The method of embodiment 11, wherein controlled release is a delivery methodology comprising subcutaneous infusion, subcutaneous depot, intravenous infusion, gastro-intestinal delivery, transmucosal delivery, or transdermal patch delivery.

Embodiment 13

The method of embodiment 11, wherein controlled release comprises subcutaneous infusion.

Embodiment 14

The method of any one of embodiments 1-13, wherein the agonist is a high potency agonist.

Embodiment 15

The method of any one of embodiments 1-13, wherein the CRFR2 agonist comprises a sequence selected from the group consisting of SEQ ID NOs: 1, 2, 3, 4, 5, 6, 7, and 8.

Embodiment 16

The method of any one of embodiments 1-13, wherein the CRFR2 agonist comprises SEQ ID NO: 1.

Embodiment 17

The method of any one of embodiments 1-16, wherein the minimum plasma concentration, the duration of a treatment period, the number of separate treatment periods, and/or the administration rate are adjusted to account for the potency of the CRFR2 agonist being utilized.

Embodiment 18

The method of any one of embodiments 1-17, wherein the duration of a treatment period, and/or the number of separate treatment periods are adjusted to account for severity of symptoms in the FSS being treated.

Embodiment 19

The method of any one of embodiments 1-18, wherein the patient is an adult.

Embodiment 20

The method of any one of embodiments 1-18, wherein the patient is a child.

Embodiment 21

The method of any one of embodiments 1-20, wherein the FSS is systemic exertion intolerance disease (SEID).

Embodiment 22

The method of any one of embodiments 1-20, wherein the FSS is fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), or Gulf War Illness (GWI, or Gulf War Syndrome).

Embodiment 23

The method of any one of embodiments 1-20, wherein the FSS is non-ulcer dyspepsia, premenstrual syndrome, chronic pelvic pain, interstitial cystitis, low back pain, repetitive strain injury, atypical chest pain, non-cardiac chest pain, hyperventilation syndrome, tension headache, temporomandibular joint disorder, atypical facial pain, Globus syndrome, food hypersensitivity, or sick building syndrome.

Embodiment 24

The method of any one of embodiments 1-20, wherein the FSS is chronic pain, anxiety, or addiction.

Embodiment 25

The method of any one of embodiments 1-20, wherein the FSS presents with the symptoms of dysautonomia.

Embodiment 26

The method of embodiment 25, wherein the dysautonomic symptoms result from primary dysautonomia.

Embodiment 27

The method of embodiment 26, wherein the primary dysautonomia is postural orthostatic tachycardia syndrome, neurocardiogenic syncope, multiple system atrophy, or Holmes-Adie syndrome.

Embodiment 28

The method of embodiment 26, wherein the primary disautonomia is a hereditary sensory and autonomic neuropathy.

Embodiment 29

The method of embodiment 25, wherein the dysautonomic symptoms result from secondary dysautonomia.

Embodiment 30

The method of embodiment 29, wherein the secondary dysautonomia presents with the symptoms of an autoimmune disease.

Embodiment 31

The method of embodiment 30, wherein the autoimmune disease is selected from the group consisting of lupus, multiple sclerosis, inflammatory bowel disease, rheumatoid arthritis, diabetes (type 1), celiac disease, Sjogren's syndrome, and Parkinson's disease.

Embodiment 32

A method for determining the extent of a stress-induced maladaptation in a human subject, comprising:
measuring a physiological parameter in the human subject, wherein the physiological parameter is selected from the group consisting of heart rate, blood pressure, and body temperature;
administering a certain concentration of an initial body weight adjusted bolus dose of a CRFR2 agonist and at least one or more subsequent bolus doses of the CRFR2 agonist, wherein the concentration of the CRFR2 agonist escalates in the one or more subsequent bolus doses;
measuring the physiological parameter in the human subject following administration of the initial bolus dose and the one or more subsequent bolus doses;
identifying the concentration of the CRFR2 agonist where a change in the physiological parameter is first measured, thereby determining a minimum stimulating bolus dose of the CRFR2 agonist necessary to induce a change in the physiological parameter; and
comparing the minimum stimulating bolus dose of the CRFR2 agonist in the subject to a reference minimum stimulating bolus dose of the CRFR2 agonist for the physiological parameter, thereby determining the extent of the stress-induced maladaptation in the human subject.

Embodiment 33

The method of embodiment 32, wherein the CRFR2 agonist comprises a sequence selected from the group consisting of SEQ ID NOs: 1, 2, 3, 4, 5, 6, 7, and 8.

Embodiment 34

The method of embodiment 32, wherein the CRFR2 agonist comprises SEQ ID NO: 1.

Embodiment 35

The method of any one of embodiments 32-34, wherein the initial bolus dose is a body weight adjusted bolus dose selected from the group consisting of about 0.01 µg/kg, about 0.02 µg/kg, about 0.03 µg/kg, about 0.04 µg/kg, about 0.05 µg/kg, about 0.06 µg/kg, about 0.07 µg/kg, about 0.08 µg/kg, about 0.09 µg/kg, and about 0.10 µg/kg.

Embodiment 36

The method of any one of embodiments 32-34, wherein the initial bolus dose is a body weight adjusted bolus dose of about 0.05 µg/kg.

Embodiment 37

The method of any one of embodiments 32-34, wherein the at least one or more subsequent bolus dose is a body weight adjusted bolus dose selected from the group consisting of about 0.06 µg/kg, about 0.07 µg/kg, about 0.08 µg/kg, about 0.09 µg/kg, about 0.10 µg/kg, about 0.11 µg/kg, about 0.12 µg/kg, about 0.13 µg/kg, about 0.14 µg/kg, about 0.15 µg/kg, about 0.16 µg/kg, about 0.17 µg/kg, about 0.18 µg/kg, about 0.19 µg/kg, and about 0.20 µg/kg.

Embodiment 38

The method of any one of embodiments 32-37, wherein the stress-induced maladaptation is a FSS.

Embodiment 39

The method of any one of embodiments 32-37, wherein the stress-induced maladaptation is systemic exertion intolerance disease (SEID).

Embodiment 40

The method of any one of embodiments 32-37, wherein the stress-induced maladaptation is fibromyalgia syndrome (FMS), post-traumatic stress disorder (PTSD), irritable bowel syndrome (IBS), atypical depression, multiple chemical sensitivity (MCS), chronic Lyme disease (CLD), pediatric acute-onset neuropsychiatric syndrome (PANS), pediatric autoimmune neuropsychiatric disorder associated with Streptococcal infections (PANDAS), or Gulf War Illness (GWI, sometimes Gulf War Syndrome).

Embodiment 41

The method of any one of embodiments 32-37, wherein the stress-induced maladaptation is non-ulcer dyspepsia, premenstrual syndrome, chronic pelvic pain, interstitial cystitis, low back pain, repetitive strain injury, atypical chest pain, non-cardiac chest pain, hyperventilation syndrome, tension headache, temporomandibular joint disorder, atypical facial pain, Globus syndrome, food hypersensitivity, or sick building syndrome.

Embodiment 42

The method of any one of embodiments 32-37, wherein the stress-induced maladaptation is chronic pain, anxiety, or addiction.

Embodiment 43

The method of any one of embodiments 32-37, wherein the stress-induced maladaptation is primary dysautonomia or secondary dysautonomia.

Embodiment 44

A method for treating a Functional Somatic Syndrome (FSS) presenting with the symptoms of dysautonomia comprising administering to a human patient in need of such treatment an effective amount of a corticotropin-releasing factor receptor subtype 2 (CRFR2) agonist.

Embodiment 45

The method of embodiment 44, wherein the dysautonomic symptoms result from primary dysautonomia.

Embodiment 46

The method of embodiment 45, wherein the primary dysautonomia is postural orthostatic tachycardia syndrome, neurocardiogenic syncope, multiple system atrophy, or Holmes-Adie syndrome.

Embodiment 47

The method of embodiment 45, wherein the primary dysautonomia is a hereditary sensory and autonomic neuropathy.

Embodiment 48

The method of embodiment 44, wherein the dysautonomic symptoms result from secondary dysautonomia presenting with the symptoms of an autoimmune disease.

Embodiment 49

The method of embodiment 48, wherein the autoimmune disease is lupus, multiple sclerosis, inflammatory bowel disease, celiac disease, or Sjogren's syndrome.

Embodiment 50

The method of embodiment 44, wherein the CRFR2 agonist comprises a sequence selected from the group consisting of SEQ ID NOs: 1, 2, 3, 4, 5, 6, 7, and 8.

Embodiment 51

The method of embodiment 44, wherein the CRFR2 agonist comprises SEQ ID NO: 1.

Embodiment 52

The method of any one of embodiments 44-51, wherein the administering is effective to achieve a minimum plasma concentration of the CRFR2 agonist greater than the minimum endocytotic concentration of the CRFR2 agonist in the human patient, and wherein the minimum plasma concentration is maintained over at least one treatment period.

Embodiment 53

The method of embodiment 52, wherein the minimum plasma concentration of the CRFR2 agonist is at least about 1.1-1.9 ng/ml.

Embodiment 54

The method of any one of embodiments 3, 10, or 53, wherein the CRFR2 agonist is a high potency CRFR2 agonist.

What is claimed is:

1. A method for treating a human patient afflicted with systemic exertion intolerance disease, the method comprising administering to the human patient in need of such treatment a corticotropin-releasing factor receptor subtype 2 (CRFR2) agonist by continuous dosing at a body weight adjusted dose of 0.8 micrograms per kilogram (μg/kg) to 1.3 μg/kg of the CRFR2 agonist, wherein the CRFR2 agonist comprises SEQ ID NO: 1 the amino acid sequence of and a minimum plasma concentration of the CRFR2 agonist is maintained at a greater level than a minimum endocytotic concentration of the CRFR2 agonist in the human patient over at over at least one treatment period of least two hours.

2. The method of claim 1, wherein the CRFR2 agonist is administered to the human patient for no more than 24 hours.

3. The method of claim 1, wherein the CRFR2 agonist is administered to the human patient over 2 to 6 treatment periods.

4. The method of claim 1, wherein the CRFR2 agonist is administered at a rate that does not increase plasma concentration of the CRFR2 agonist in the human patient by more than a maximum rate of 0.2 ng/ml in any 15-minute time window within any treatment period.

5. The method of claim 1, wherein the body weight adjusted dose of the CRFR2 agonist is 0.8 μg/kg to 1.1 μg/kg of the CRFR2 agonist.

6. The method of claim 1, wherein the body weight adjusted dose of the CRFR2 agonist is administered as a bolus followed by a controlled release.

7. The method of claim 1, wherein the body weight adjusted dose of the CRFR2 agonist is administered to achieve a plasma concentration of 1.1 nanograms per milliliter (ng/ml) to 1.9 ng/ml in the human patient.

8. The method of claim 1, wherein the body weight adjusted dose of the CRFR2 agonist is administered to achieve a plasma concentration of 1.1 ng/ml to 1.6 ng/ml in the human patient.

9. The method of claim 1, wherein the body weight adjusted dose of the CRFR2 agonist is administered to achieve an area under the curve for the plasma concentration over time of 6 nanogram hours per milliliter (ngh/ml) to 8 ngh/ml.

10. The method of claim 1, wherein the body weight adjusted dose of the CRFR2 agonist is administered to achieve an area under the curve for the plasma concentration over time of about 7 ngh/ml.

11. A method for treating a human patient afflicted with systemic exertion intolerance disease, the method comprising administering to the human patient in need of such treatment a corticotropin-releasing factor receptor subtype 2 (CRFR2) agonist by continuous dosing for least two hours and for no longer than 12 hours and at a plasma concentration of 1.1 nanograms per milliliter (ng/ml) to 1.9 ng/ml of the CRFR2 agonist in the human patient, wherein the CRFR2 agonist comprises SEQ ID NO: 1 the amino acid sequence of and a minimum plasma concentration of the CRFR2 agonist is maintained at a greater level than a minimum endocytotic concentration of the CRFR2 agonist in the human patient.

* * * * *

SEQUENCE LISTING

```
<160> NUMBER OF SEQ ID NOS: 8

<210> SEQ ID NO 1
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Asp Thr Ile
```

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
            35                  40

<210> SEQ ID NO 3
<211> LENGTH: 40
<212> TYPE: PRT
<213> ORGANISM: Homo sapiens

<400> SEQUENCE: 3

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
            35                  40

<210> SEQ ID NO 4
<211> LENGTH: 38
<212> TYPE: PRT
<213> ORGANISM: Homo sapiens

<400> SEQUENCE: 4

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
            35

<210> SEQ ID NO 5
<211> LENGTH: 43
<212> TYPE: PRT
<213> ORGANISM: Homo sapiens

<400> SEQUENCE: 5

His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Ala Arg Glu Gln
            20                  25                  30

Ala Thr Thr Asn Ala Arg Ile Leu Ala Arg Val
            35                  40

<210> SEQ ID NO 6
<211> LENGTH: 38
<212> TYPE: PRT
<213> ORGANISM: Homo sapiens

```
<400> SEQUENCE: 6

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 7
<211> LENGTH: 40
<212> TYPE: PRT
<213> ORGANISM: Homo sapiens

<400> SEQUENCE: 7

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glx or Pyrrolidone carboxylic acid
<220> FEATURE:
<221> NAME/KEY: MOD_RES
<222> LOCATION: (11)..(11)
<223> OTHER INFORMATION: Phe, Tyr, Leu, Ile or Thr
<220> FEATURE:
<221> NAME/KEY: MOD_RES
<222> LOCATION: (12)..(12)
<223> OTHER INFORMATION: Gln, Trp or Tyr
<220> FEATURE:
<221> NAME/KEY: MOD_RES
<222> LOCATION: (17)..(17)
<223> OTHER INFORMATION: Val or Met
<220> FEATURE:
<221> NAME/KEY: MOD_RES
<222> LOCATION: (31)..(31)
<223> OTHER INFORMATION: Thr or Ala
<220> FEATURE:
<221> NAME/KEY: MOD_RES
<222> LOCATION: (32)..(32)
<223> OTHER INFORMATION: Asn or Thr
<220> FEATURE:
<221> NAME/KEY: MOD_RES
<222> LOCATION: (35)..(35)
<223> OTHER INFORMATION: Arg or Leu
<220> FEATURE:
<221> NAME/KEY: MOD_RES
<222> LOCATION: (36)..(36)
<223> OTHER INFORMATION: Leu or Ile
<220> FEATURE:
<221> NAME/KEY: MOD_RES
<222> LOCATION: (38)..(38)
<223> OTHER INFORMATION: Asp or Ala
<220> FEATURE:
<221> NAME/KEY: MOD_RES
<222> LOCATION: (39)..(39)
<223> OTHER INFORMATION: Thr or Arg
<220> FEATURE:
<221> NAME/KEY: MOD_RES
<222> LOCATION: (40)..(40)
```

-continued

```
<223> OTHER INFORMATION: Ile or Val
<220> FEATURE:
<223> OTHER INFORMATION: See specification as filed for detailed
      description of substitutions and preferred embodiments

<400> SEQUENCE: 8

Glx Gly Pro Pro Ile Ser Ile Asp Leu Pro Xaa Xaa Leu Leu Arg Lys
1               5                   10                  15

Xaa Ile Glu Ile Glu Lys Gln Glu Lys Glu Lys Gln Gln Ala Xaa Xaa
            20                  25                  30

Asn Ala Xaa Xaa Leu Xaa Xaa Xaa
        35                  40
```